US008524772B2

(12) United States Patent
Arad et al.

(10) Patent No.: US 8,524,772 B2
(45) Date of Patent: Sep. 3, 2013

(54) CONTROLLED RELEASE OF N-ACETYLCYSTEINE (NAC) FOR REDUCTION OF SYSTEMIC AND/OR VASCULAR INFLAMMATION

(75) Inventors: Yadon Arad, Sunnyvale, CA (US); Liang C. Dong, Sunnyvale, CA (US)

(73) Assignee: Tiara Pharmaceuticals, Inc., Los Altos, CA (US)

( * ) Notice: Subject to any disclaimer, the term of this patent is extended or adjusted under 35 U.S.C. 154(b) by 0 days.

(21) Appl. No.: 12/595,027

(22) PCT Filed: May 11, 2009

(86) PCT No.: PCT/US2009/043435
§ 371 (c)(1),
(2), (4) Date: Jun. 16, 2011

(87) PCT Pub. No.: WO2009/137827
PCT Pub. Date: Nov. 12, 2009

(65) Prior Publication Data
US 2011/0244045 A1     Oct. 6, 2011

Related U.S. Application Data

(60) Provisional application No. 61/052,120, filed on May 9, 2008, provisional application No. 61/143,105, filed on Jan. 7, 2009.

(51) Int. Cl.
*A61K 31/225* (2006.01)

(52) U.S. Cl.
USPC .......................... 514/547; 514/550; 514/562

(58) Field of Classification Search
USPC ......................................... 514/547, 550, 562
See application file for complete search history.

(56) References Cited

U.S. PATENT DOCUMENTS

| | | | |
|---|---|---|---|
| 4,612,008 A | 9/1986 | Wong et al. | |
| 4,871,548 A | 10/1989 | Edgren et al. | |
| 4,894,240 A | 1/1990 | Geoghegan et al. | |
| 5,401,514 A * | 3/1995 | Juch et al. | 424/465 |
| 5,445,829 A * | 8/1995 | Paradissis et al. | 424/480 |
| 5,637,616 A | 6/1997 | Sharpe et al. | |
| 5,785,994 A * | 7/1998 | Wong et al. | 424/473 |
| 6,207,190 B1 * | 3/2001 | Richardson et al. | 424/472 |
| 6,368,626 B1 * | 4/2002 | Bhatt et al. | 424/473 |
| 6,369,106 B1 * | 4/2002 | Atlas et al. | 514/547 |
| 7,074,825 B2 * | 7/2006 | Mo et al. | 514/456 |
| 2004/0018996 A1 | 1/2004 | Richardson et al. | |
| 2007/0049641 A1 | 3/2007 | Tirouvanziam et al. | |
| 2008/0091176 A1 | 4/2008 | Alessi et al. | |
| 2008/0095806 A1 | 4/2008 | Bathurst et al. | |

FOREIGN PATENT DOCUMENTS

WO     WO-95/29666     * 11/1995

OTHER PUBLICATIONS

Hayashi et al., "HMG CoA reductase inhibitors reduce ischemic brain injury of Wistar rats through decreasing oxidative stress on neurons", 2005, Brain Research, vol. 1037, pp. 52-58.*

Young, "International Search Report," 2 pages, from International Appl. No. PCT/US09/43435, United States Patent and Trademark Office, Alexandria, Virginia, USA (mailed Aug. 18, 2009).
Young, "Written Opinion of the International Searching Authority," 7 pages, from International Appl. No. PCT/US09/43435, United States Patent and Trademark Office, Alexandria, Virginia, USA (mailed Aug. 18, 2009).
Alipour et al., "Prophylactic effect of liposomal N-acetylcysteine against LPS-induced liver injuries," J. Endotoxin Res. 13(5):297-304 (2007).
Aoyama et al., Oxidative stress on EAAC1 is involved in MPTP-induced glutathione depletion and motor dysfunction. Eur J Neurosci. Dec. 14, 2007.
Bisoendial et al., "C-reactive protein and atherogenesis: From fatty streak to clinical event," Atherosclerosis 195(2):e10-e18 (2007).
Chang et al., "C-Reactive Protein Induces NF-κB Activation through Intracellular Calcium and ROS in Human Mesangial Cells," Nephron Exp. Nephrol. 101(4):e165-e172 (2005).
Chen et al., "Antioxidative and anti-inflammatory effects of four cysteine-containing agents in striatum of MPTP-treated mice," Nutrition 23(7-8):589-597 (2007).
Chuang et al., "N-acetylcysteine attenuates the acute lung injury caused by phorbol myristate acetate in isolated rat lungs," Pulm. Pharmacol. Ther. 20(6):726-733 (2007).
de Ferranti and Rifai, "C-reactive protein: a nontraditional serum marker of cardiovascular risk," Cardiovasc. Pathol. 16(1):14-21 (2007).
Devaraj et al., "Statins and Biomarkers of Inflammation," Curr. Atheroscler. Rep. 9(1):33-41 (2007).
Fu et al., "Protective effect of N-acetyl-L-cysteine on amyloid β-peptide-induced learning and memory deficits in mice," Brain Res. 1109(1):201-206 (2006).
Fujii et al., "C-Reactive Protein Alters Antioxidant Defenses and Promotes Apoptosis in Endothelial Progenitor Cells," Arterioscler. Thromb. Vasc. Biol. 26(11):2476-2482 (2006).
Galis et al., "N-Acetyl-Cysteine Decreases the Matrix-Degrading Capacity of Macrophage-Derived Foam Cells: New Target for Antioxidant Therapy?" Circulation 97(24):2445-2453 (1998).
Gonzalez-Gay et al., "High-grade C-Reactive Protein Elevation Correlates with Accelerated Atherogenesis in Patients with Rheumatoid Arthritis," J. Rheumatol. 32(7):1219-1223 (2005).
Gotto, Jr., "Role of C-Reactive Protein in Coronary Risk Reduction: Focus on Primary Prevention," Am. J. Cardiol. 99(5):718-725 (2007).
Hicdonmez et al., "Neuroprotective Effects of N-acetylcysteine on Experimental Closed Head Trauma in Rats," Neurochem. Res. 31(4):473-481 (2006).
Inoue, "Vascular C-reactive protein in the pathogenesis of coronary artery disease: role of vascular inflammation and oxidative stress," Cardiovasc. Hematol. Disord. Drug Targets 6(4):227-231 (2006).

(Continued)

*Primary Examiner* — Ali Soroush
(74) *Attorney, Agent, or Firm* — Cooley LLP

(57) ABSTRACT

The present invention provides a controlled-release composition which provides a therapeutically effective plasma concentration of N-acetylcysteine over prolonged period of time. The present invention also includes the use of the controlled-release composition, either alone or in combination with at least one additional active agent, for reduction of vascular inflammation marker and treatment of diseases, conditions, and/or symptoms associated with systemic and/or vascular inflammation in a patient. Furthermore, the present invention provides a process of making granules comprising N-acetylcysteine, or a salt, solvate, prodrug, and/or analog thereof.

43 Claims, 4 Drawing Sheets

(56) References Cited

OTHER PUBLICATIONS

Ivanovski et al., "The antioxidant N-acetylcysteine prevents accelerated atherosclerosis in uremic apolipoprotein E knockout mice," Kidney Int. 67(6):2288-2294 (2005).

Jara-Prado et al., "Homocysteine-Induced Brain Lipid Peroxidation: Effects of NMDA Receptor Blockade, Antioxidant Treatment, and Nitric Oxide Synthase Inhibition," Neurotox. Res. 5(4):237-243 (2003).

Jialal et al., "C-Reactive Protein: Risk Marker or Mediator in Atherothrombosis?" Hypertension 44(1):6-11 (2004).

Karageorgos et al., "Effect of N-acetylcysteine, allopurinol and vitamin E on jaundice-induced brain oxidative stress in rats," Brain Res. 1111(1):203-212 (2006).

Kaya et al., The protective effect of N-acetylcysteine against cyclosporine A-induced hepatotoxicity in rats. J Appl Toxicol. Jan.-Feb. 2008;28(1):15-20 (2008).

Kim-Han and O'Malley, "Cell Stress Induced by the Parkinsonian Mimetic, 6-Hydroxydopamine, is Concurrent with Oxidation of the Chaperone, ERp57, and Aggresome Formation," Antioxid. Redox. Signal, 9(12):2255-2264 (2007).

Koksel et al., "N-acetylcysteine inhibits peroxynitrite-mediated damage in oleic acid-induced lung injury," Pulm. Pharmacol. Ther. 17(5):263-270 (2004).

Krieger et al., "Antiatherogenic effects of S-nitroso-N-acetylcysteine in hypercholesterolemic LDL receptor knockout mice," Nitric Oxide 14(1):12-20 (2006).

Liu et al., "Antioxidant N-acetylcysteine attenuates the acute liver injury caused by X-ray in mice," Eur. J. Pharmacol. 575(1-3):142-148 (2007).

Molnar et al., "Prophylactic N-acetylcysteine decreases serum CRP but not PCT levels and microalbuminuria following major abdominal surgery. A prospective, randomised, double-blinded, placebo-controlled clinical trial," Intensive Care Med. 29(5):749-755 (2003).

Mora and Ridker, "Justification for the Use of Statins in Primary Prevention: An Intervention Trial Evaluating Rosuvastatin (Jupiter)—Can C-reactive Protein Be Used to Target Statin Therapy in Primary Prevention?" Am. J. Cardiol. 97(2A):33A-41A (2006).

Nissen, "Effect of Intensive Lipid Lowering on Progression of Coronary Atherosclerosis: Evidence for an Early Benefit from the Reversal of Atherosclerosis with Aggressive Lipid Lowering (Reversal) Trial," Am. J. Cardiol. 96(5A):61F-68F (2005).

Paffen and DeMaat, "C-reactive protein in atherosclerosis: A causal factor?" Cardiovasc. Res. 71(1):30-39 (2006).

Penugonda et al., "Effects of N-acetylcysteine amide (NACA), a novel thiol antioxidant against glutamate-induced cytotoxicity in neuronal cell line PC12," Brain Res. 1056(2):132-138 (2005).

Prasad, "C-Reactive Protein (CRP)-Lowering Agents," Cardiovasc. Drug Rev. 24(1):33-50 (2006).

Price et al., "A novel antioxidant N-acetylcysteine amide prevents gp120-and Tat-induced oxidative stress in brain endothelial cells," Exp. Neurol. 201(1):193-202 (2006).

Rattan and Arad, "Temporal and kinetic determinants of the inhibition of LDL oxidation by N-acetylcysteine (NAC)," Atherosclerosis 138(2):319-327 (1998).

Shavali and Sens, "Synergistic Neurotoxic Effects of Arsenic and Dopamine in Human Dopaminergic Neuroblastoma SH-SY5Y Cells," Toxicol. Sci. 102(2):254-261 (2007).

Shea, "Effects of Dietary Supplementation with N-Acetyl Cysteine, Acetyl-L-Carnitine and S-Adenosyl Methionine on Cognitive Performance and Aggression in Normal Mice and Mice Expressing Human Apoe4," Neuromolecular Med. 9(3):264-269 (2007).

Sjödin et al., "Metabolism of N-Acetyl-L-Cysteine. Some Structural Requirements for the Deacetylation and Consequences for the Oral Bioavailability," Biochem. Pharmacol. 38(22):3981-3985 (1989).

Tchantchou et al., "Dietary Supplementation With 3-Deaza Adenosine, N-Acetyl Cysteine, and S-Adenosyl Methionine Provide Neuroprotection Against Multiple Consequences of Vitamin Deficiency and Oxidative Challenge: Relevance to Age-Related Neurodegeneration," Neuromolecular Med. 6(2-3):93-103 (2004).

Van Antwerpen et al., "Thiol-containing molecules interact with the myeloperoxidase/$H_2O_2$/chloride system to inhibit LDL oxidation," Biochem. Biophys. Res. Commun. 337(1):82-88 (2005).

Venugopal et al., "Effect of C-reactive protein on vascular cells: evidence for a proinflammatory, proatherogenic role," Curr. Opin. Nephrol. Hypertens. 14(1):33-37 (2005).

Wagberg et al., "N,N'-Diacetyl-L-cystine (DiNAC), the Disulphide Dimer of N-Acetylcysteine, Inhibits Atherosclerosis in WHHL Rabbits: Evidence for Immunomodulatory Agents as a New Approach to Prevent Atherosclerosis," J. Pharmacol. Exp. Ther. 299(1):76-82 (2001).

Wilson et al., "The novel role of C-reactive protein in cardiovascular disease: Risk marker or pathogen," Int. J. Cardiol. 106(3):291-297 (2006).

Zambon et al., "Modulation of Hepatic Inflammatory Risk Markers of Cardiovascular Diseases by PPAR-α Activators: Clinical and Experimental Evidence," Arterioscler. Thromb. Vasc. Biol. 26(5):977-986 (2006).

Zuin et al., "High-Dose N-Acetylcysteine in Patients With Exacerbations of Chronic Obstructive Pulmonary Disease," Clin. Drug Investig. 25(6):401-408 (2005).

\* cited by examiner

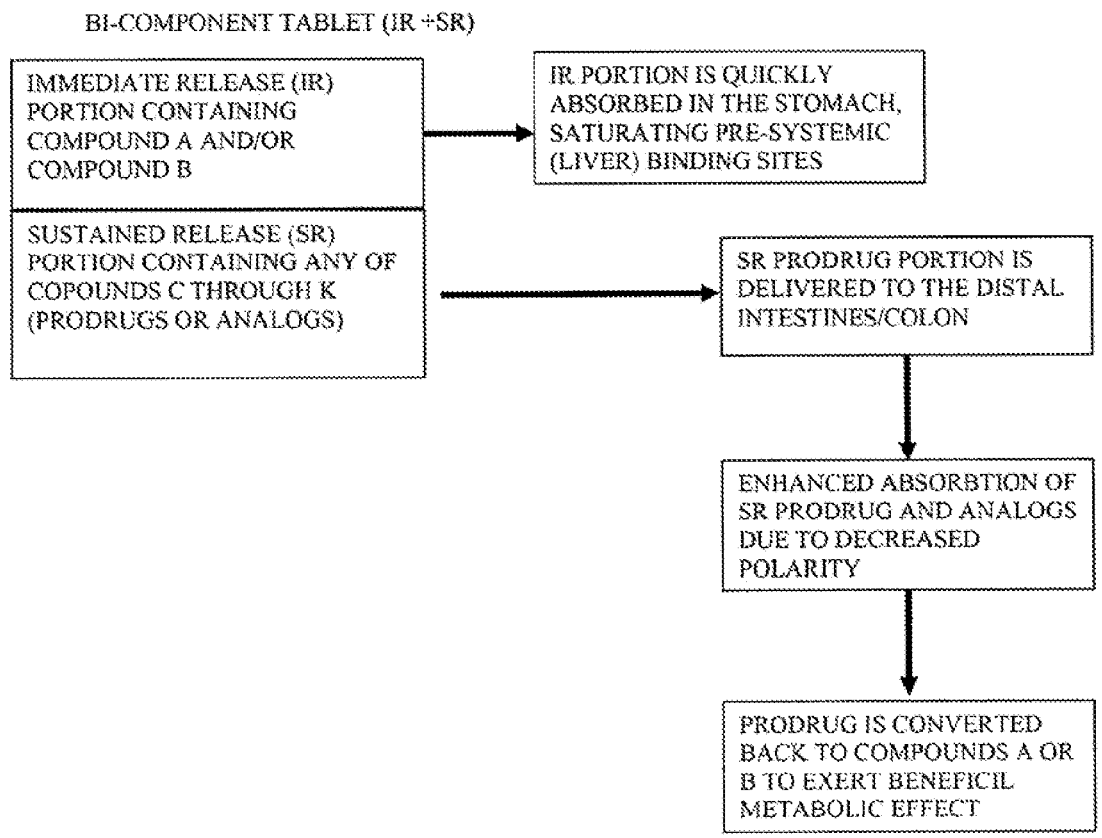
Figure 1. A Flow Diagram of the Bi-modal Tablet

Figure 2. Controlled-Release Oral Dosage Form (Matrix)
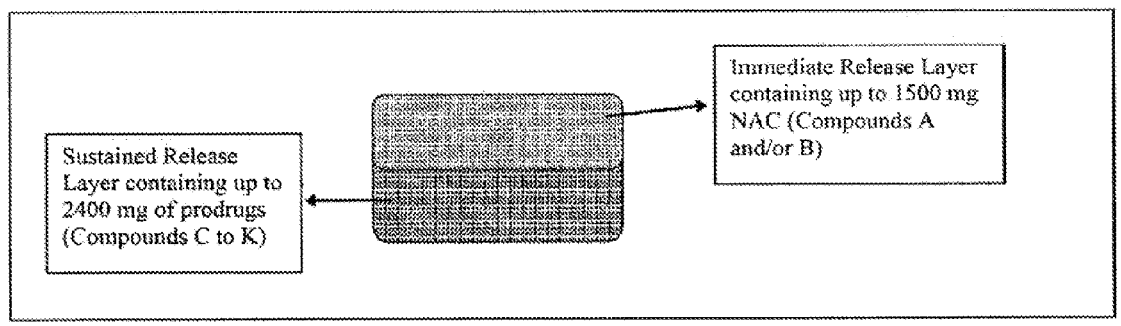

Figure 3. Controlled-Release Oral Dosage Form (Osmotic Delivery System)
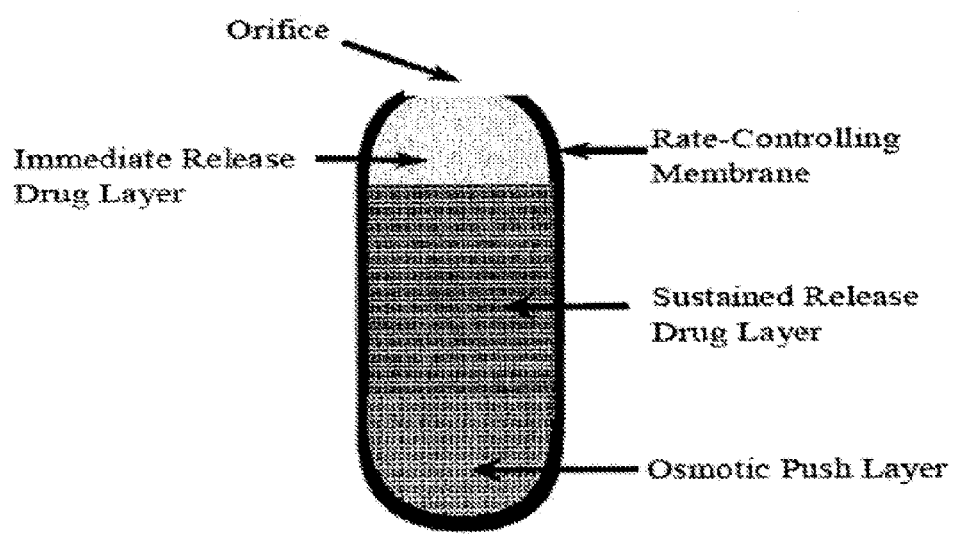

Figure 4. Controlled-Release Oral Dosage Form (Multiparticulates)
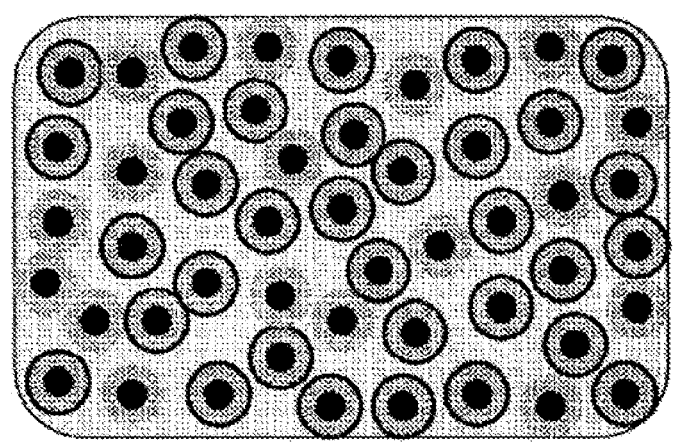
 SR sphere  IR sphere  Disintegrant

CONTROLLED RELEASE OF N-ACETYLCYSTEINE (NAC) FOR REDUCTION OF SYSTEMIC AND/OR VASCULAR INFLAMMATION

CROSS-REFERENCE TO THE RELATED APPLICATIONS

This application is a U.S. National Stage of International Application number PCT/US2009/043435, filed May 11, 2009, which claims priority to U.S. Provisional Application No. 61/052,120, filed on May 9, 2008 and entitled "Sustained Controlled Release Prodrug of N-acetylcysteine (NAC) for Reduction of Vascular Inflammatory Markers, of Systemic and Vascular Inflammation, and of Atherosclerosis and Acute Coronary Events", and U.S. Provisional Application No. 61/143,105, filed on Jan. 7, 2009 and entitled "Sustained Controlled Release Prodrug of N-acetylcysteine (NAC) for Reduction of Vascular Inflammatory Markers, of Systemic and Vascular Inflammation, and of Atherosclerosis and Acute Coronary Events", the disclosures of which are herein incorporated by reference in their entirety for all purposes.

FIELD OF INVENTION

The present invention is related to a combination of modified forms of D-NAC and/or L-NAC including the salts and/or solvates thereof, together with a controlled-release composition to provide a therapeutically effective plasma concentration of N-acetylcysteine over prolonged period of time.

BACKGROUND

Atherosclerosis is a long-term chronic inflammatory disease which is associated with increased concentrations of various inflammatory markers, including the hepatic-origin C-reactive peptide ("CRP") (Zambon et al., 2006). CRP has been identified not only as a very sensitive marker and risk factor for atherosclerosis, but also as a pro-inflammatory mediator which is involved in endothelial cell dysfunction, oxidant stress, and intimal hypertrophy, leading to plaque rupture and myocardial infarction. (Wilson et al., 2006; Mora et al., 2006; Paffen et al., 2006; Inoue, 2006; de Ferranti, et al., 2007; Gotto et al., 2007; Bisoendial et al., 2007; and Gonzalez-Gay, et al., 2005)

Evidence for the direct causal role of CRP in atherosclerosis includes its ability to induce matrix metalloproteinase-1 ("MMP-1") expression through the Fc gamma RII and extra cellular signal-related kinase pathways (shown in U937 cells). MMP-1, in turn, are implicated in plaque instability. Additionally, CRP is shown to up-regulate interleukin-1, interleukin-6, and interleukin-8 in human aortic endothelial cells via nuclear factor-kappa B. CRP also promotes monocyte chemoattractant protein-1-mediated chemotaxis by up regulating CC-chemokine receptor 2 expression in human monocytes. CRP is also shown to attenuate endothelial progenitor cell survival, differentiation, and function. (Venugopal et al., 2005)

Other proinflammatory, proatherogenic effects of CRP on endothelial cells include the following: decreased endothelial-derived nitric oxide and prostacyclin versus increased endothelin-1, cell adhesion molecules, monocyte chemoattractant protein-1 and plasminogen activator inhibitor-1 (leading to higher likelihood for a blood clot). In monocyte-macrophages, CRP may induce tissue factor secretion, increase reactive oxygen species and proinflammatory cytokine release, promote monocyte chemotaxis and adhesion, and increase oxidized low-density lipoprotein uptake. Also, CRP has been shown in vascular smooth muscle cells to increase inducible nitric oxide production (thought to be detrimental as opposed to endothelial-derived nitric oxide), increase NFkappa-b and mitogen-activated protein kinase activities, and, importantly, up regulate angiotensin type-1 receptor resulting in increased reactive oxygen species and vascular smooth muscle cell proliferation. (halal et al., 2004; and Chang et al., 2005)

N-acetylcysteine (NAC) is an antioxidant and a thiol donor. Currently, NAC is clinically used for treatment of hepatotoxicity caused by acetaminophen overdose, for treatment of chronic bronchitis and other pulmonary diseases complicated by the production of viscous mucus, and for treatment of reperfusion injury during cardio bypass surgery. The protective effects of NAC against inflammatory/oxidative challenges were also demonstrated in various animal models of brain injury, (Fu et al., 2006; Hicdonmez, et al., 2006; Jara-Prado et al., 2003; Karageorgos, et al., 2006; Penugonda et al., 2005; Price et al., 2006; Shea, 2007; and Tchantchou et al., 2004) liver injury, (Kaya et al., 2008; Liu et al., 2007; and Alipour et al., 2007) and lung injury (e.g. LPS-induced, TNF-mediated MPO increase and apoptosis) (Koksel et al., 2004; Chuang et al., 2007; and Chen et al., 2007) In vitro, NAC also inhibited the oxidative modification of LDL. (Van Antwerpen et al., 2005) In particular, secondary oxidation of LDL by previously oxidized LDL was markedly inhibited, (Rattan et al., 1998) an effect not seen with other antioxidants. NAC was also shown to reduce the ability of lipid loaded macrophages (foam cells) to degrade vascular matrix. (Galis, et al., 1998)

Several animal models have actually demonstrated inhibition of atherosclerosis by NAC. (Fujii et al., 2006; Krieger et al., 2006; Ivanovski et al., 2005; and Wagberg et al., 2001) Based on the data cited above, CRP may be a suitable target for therapy to reduce atherosclerosis. However, currently there is no specific therapy to lower CRP concentration. Although statin therapy, some ACE inhibitors and ARBs, anti-inflammatory drugs, and perhaps fish oils have some benefits, (Prasad et al., 2006; Devarai et al., 2007; and Nissen, 2005) their benefit is limited, and difficult to assess because of their other biochemical effects, and many are associated with undesirable side effects.

In addition to the cell cultures studies (cited above) demonstrating the protective effects on NAC against CRP-mediated inflammation, an immediate release form of NAC has been recently demonstrated to lower CRP serum concentrations. Intravenous NAC was administered to patients undergoing abdominal surgery. CRP level following the surgery fell by 30% as compared to placebo infusion. (Molnar et al., 2003) Even more impressively, Patients with exacerbation of chronic obstructive pulmonary disease (COPD) demonstrated an increase in CRP but orally administered NAC resulted in decreased CRP (CRP normalized in 52% of patients on 600 mg/day and 90% of patients on 600 mg twice a day). The apparent greater efficacy of oral NAC vs. intravenous NAC may be related to the increased liver delivery of NAC via the oral route. (Zuin et al., 2005) Therefore, NAC is a very appealing therapeutic agent for achieving a reduction in CRP, thereby reducing inflammation and oxidative damage, and for the prevention/treatment of atherosclerosis and possibly other inflammatory and/or oxidative insults in other diseases such as Parkinson's disease (note its benefit in MPTP-induced Parkinson's disease and other models). (Penugonda et al., 2005; Aoyama et al., 2007; Shavali et al., 2007; and Kim-Han et al., 2007)

SUMMARY OF THE INVENTION

In one embodiment, the present invention provides a composition comprising a sustained release (SR) component, wherein the SR component comprises N-acetylcysteine, or a salt, solvate, prodrug, and/or analog thereof; wherein the composition, upon oral administration, provides a therapeutically effective plasma concentration of N-acetylcysteine over about 2 to about 24 hours following the administration. The prodrug and/or analog decreases the polarity of NAC to increase its absorption in the lower GI tract, such as the large intestine, and may further be broken or decomposed into the original NAC by naturally occurring serum enzymes, such as serum esterases and amidases.

In another embodiment, the present invention provides a composition comprising an immediate release (IR) component, wherein the IR component comprises N-acetylcysteine, or a salt, solvate, prodrug, and/or analog thereof; and a sustained release (SR) component, wherein the SR component comprises N-acetylcysteine, or a salt, solvate, prodrug, and/or analog thereof; wherein the composition, upon oral administration, provides a therapeutically effective plasma concentration of N-acetylcysteine over about 30 minutes to about 24 hours following the administration.

In another embodiment, the present invention provides a method of reducing a vascular inflammatory marker or mediator in a mammal comprising orally administering to the mammal the composition of the present invention.

In another embodiment, the present invention provides a method of reducing systemic inflammation, inflammation of a particular organ, and/or vascular inflammation in a mammal comprising orally administering to the mammal the composition of the present invention.

In another embodiment, the present invention provides a method of treating a disease, condition, or symptom associated with systemic and/or vascular inflammation in a mammal comprising orally administering to the mammal the composition of the present invention.

In another embodiment, the present invention provides a method of treating a disease, condition, or symptom associated with systemic and/or vascular inflammation in a mammal comprising co-administering to the mammal (a) N-acetylcysteine, or a salt, solvate, prodrug, and/or analog thereof; and (b) at least one additional active agent.

In another embodiment, the present invention provides a composition comprising (a) N-acetylcysteine, or a salt, solvate, prodrug, and/or analog thereof; and (b) at least one additional active agent.

In another embodiment, the present invention provides a process of making granules comprising N-acetylcysteine, or a salt, solvate, prodrug, and/or analog thereof, wherein the process does not utilize a solvent.

BRIEF DESCRIPTION OF THE DRAWINGS

FIG. 1 is a flow diagram which illustrates one specific embodiment of a bi-modal tablet by providing a schematic description of how the medication is composed, absorbed and then de-esterified to achieve high concentrations of the parent compound in the circulation. The final embodiment is composed of two or more layers. One layer contains immediate release N-acetyl-L-cysteine or N-acetyl-D-cysteine and the other layers contain sustained release formulation of any of compounds C through K (described herein below). The dosage form may also be covered with enteric coating to prevent release in the stomach, thus minimizing gastric irritation. The IR layer is quickly absorbed in the small intestines, thereby saturating pre-systemic (liver) binding sites. The SR prodrug containing compound C through K is delivered to the distal intestines/colon. Due to decreased polarity, there is enhanced absorption of the SR portion in the distal intestines and colon. Following absorption, the prodrugs are broken by serum esterases, converting them back to N-acetyl-L-cysteine or N-acetyl-D-cysteine. The total process leads to higher systemic blood concentrations of NAC.

FIG. 2 is a pictorial illustration of one embodiment of a controlled release oral dosage form of N-acetylcysteine formulated to a matrix delivery system. The dosage form is composed of two or more layers, one layer contains the immediate release forms of N-acetyl-L-cysteine, N-acetyl-D-cysteine, or both, which are release fairly quickly in the stomach and small intestines. The other layers contain any of the sustained-release formulations of compounds C through K (described herein below) which are released in a slow sustained fashion to provide persistently leveled blood concentrations over about 12 to about 24 hours. Additional details are described in Example 1.

FIG. 3 is a pictorial illustration of one embodiment of a controlled release oral dosage form of N-acetylcysteine formulated to osmotic delivery system. The osmotic delivery system comprises three layers (immediate-release layer, sustained-release layer and osmotic push layer), and bound with a rate controlling cover membrane with one orifice. As fluids moves through the membrane into the capsule wall, the osmotic push layer expands and pushes out first the IR layer and then the SR layer through the orifice. Additional details are described in Example 14.

FIG. 4 is a pictorial illustration of one embodiment of a controlled release oral dosage form of N-acetylcysteine formulated as a multiparticulate delivery system. The dosage form contains N-acetyl-L-cysteine and/or N-acetyl-D-cysteine in IR particles and any of compounds C through K (described herein below) in an SR particles. The tablet disintegrates in the gastric fluid. Following disintegration, the IR particles dissolve rapidly to release the IR portion with N-acetyl-L cysteine and/or N-acetyl-D-cysteine. The SR particles travel to the distal intestines and colon, dissolving slowly over about 12 to about 24 hours. Additional details are described in Example 15.

DETAILED DESCRIPTION OF THE INVENTION

The present invention provides controlled-release compositions that can achieve sustained systemic blood concentration of N-acetylcysteine, or a salt, solvate, prodrug, and/or analog thereof, over a long period of time and thereby inhibit systemic, organ-specific, and/or vascular inflammation continuously. The composition may be formulated to provide a mono-modal or bi-modal release profile. By "mono-modal", it is meant a composition comprising a sustained-release (SR) component. The term "sustained-release" denotes the release of the active agent in a controlled or modified manner over a period of time. By "bi-modal", it is meant a composition comprising both an immediate-release (IR) component and a SR component. The bi-modal composition provides an initial burst of N-acetylcysteine, or a salt, solvate, prodrug, and/or analog thereof, for a quick build up of the systemic level of N-acetylcysteine in order to, for instance, saturate the presystemic metabolizing enzymes, followed by the sustained release of N-acetylcysteine, or a salt, solvate, prodrug, and/or analog thereof, for maintaining the therapeutic level. After the IR component quickly releases N-acetylcysteine, or a salt, solvate, prodrug, and/or analog thereof, within an hour, the SR component releases the drug thereafter over a long period of time, such as over about 1 to about 48 hours, preferably over about 2 hours to 36 hours, and more preferably over about 3 to about 24 hours for maintaining the therapeutic level of NAC. The dosage form of the composition can be administered as many times as necessary per day, but preferably twice daily or more preferably once daily. The IR component may contain from about 10 to 1500 mg of N-acetylcysteine, or a salt, solvate, prodrug, and/or analog thereof, for example about 10 mg, about 20 mg, about 30 mg, about 40 mg, about 50 mg, about 75 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 100 mg, about it and 50 mg, about 900 mg, about 950 mg, about 1000 mg, about 1100 mg, about 1200 mg, about 1300 mg, about 1400 mg, or about 1500 mg of N-acetylcysteine, or a salt, solvate, prodrug, and/or analog thereof; while the SR component may contain from about 50 to about 2400 mg of N-acetylcysteine, or a salt, solvate, prodrug, and/or analog thereof, for example about 50 mg, about 75 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 100 mg, about it and 50 mg, about 900 mg, about 950 mg, about 1000 mg, about 1100 mg, about 1200 mg, about 1300 mg, about 1400 mg, or about 1500 mg, about 1600 mg, about 1700 mg, about 1800 mg, about 1900 mg, about 2000 mg, about 2100 mg, about 2200 mg, about 2300 mg, or about 2400 mg of N-acetylcysteine, or a salt, solvate, prodrug, and/or analog thereof.

The composition may be formulated to various delivery systems including matrix delivery systems, (U.S. Pat. No. 4,871,548), osmotic delivery systems (U.S. Pat. No. 4,612,008), and mutiparticulate delivery systems (U.S. Pat. No. 4,894,240). Matrix delivery systems are known to the field of pharmaceutical drug delivery (U.S. Pat. Nos. 3,870,790; 4,140,755; 4,167,588; 4,226,849; 4,259,314; 4,357,469; 4,369,172; 4,389,393; 4,540,566 and 4,839,177, the disclosures of which are incorporated herein by reference in their entirety). The osmotic delivery systems have been reported in a number of (U.S. Pat. Nos. 4,111,202, 4,327,725, 4,612,008, 4,765,989; 4,783,337, 5,082,668, 6,919,373, the disclosures of which are incorporated herein by reference in their entirety). The multiparticulate delivery systems typically involve hard gelatin capsule or compressed tablets containing film-coated spheroids or beads, as described, for example, by U.S. Pat. Nos. 2,996,431, 3,492,397, 3,835,221, 4,138,475, 4,415,547, 4,894,240 and 6,419,958, the disclosures of which are incorporated herein by reference in their entirety. Use of ionic exchange resin for sustained release of a pharmaceutical agent has also been disclosed in U.S. Pat. Nos. 2,990,332, 3,138,525, 3,499,960, 3,594,470, and 4,894,239, the disclosures of which are incorporated herein by reference in their entirety. In addition, the controlled-release of prodrugs of carbidopa/L-dopa was disclosed in an U.S. Pat. No. 7,101,912 for treatment of Parkinson disease, the disclosures of which are incorporated herein by reference in their entirety.

As used herein, the terms "a" and "an" do not denote a limitation of quantity, but rather denote the presence of at least one of the referenced item. The term "or" means "and/or". The terms "comprising", "having", "including", and "containing" are to be construed as open-ended terms (i.e., meaning "including, but not limited to") unless otherwise noted. The terms "optional" and "optionally" means possible/possibly, but not necessary/necessarily.

N-Acetylcysteine and Modified N-Acetylcysteine

As used herein, the term "N-acetylcysteine", also known as 2-acetamido-3-sulfanylpropanoic acid or NAC, refers to a compound having a structure shown in Scheme 1 and includes N-acetyl-L-cysteine (Compound A), i.e., (2R)-2-acetamido-3-sulfanylpropanoic acid; N-acetyl-D-cysteine (Compound B), i.e., (2R)-2-acetamido-3-sulfanylpropanoic acid); and a mixture of N-acetyl-L-cysteine and N-acetyl-D-cysteine in any ratio. Similarly, the term "cysteine" as used herein comprises L-cysteine, D-cysteine, and a mixture thereof.

N-acetyl-D-cysteine is more resistant to gastrointestinal degradation or biological metabolization as compared to N-acetyl-L-cysteine, thus it may be advantageous to use the D form N-acetyl-D-cysteine in the present compositions. In one embodiment of the present composition, the IR and/or SR component(s) comprises N-acetyl-D-cysteine, or a salt, solvate, prodrug, and/or analog thereof.

Scheme 1:

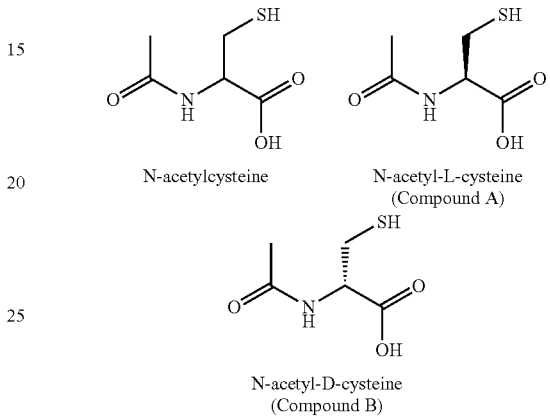

N-acetylcysteine

N-acetyl-L-cysteine
(Compound A)

N-acetyl-D-cysteine
(Compound B)

"Analog" refers to a compound, the chemical structure and/or therapeutic effect of which are related to or similar to N-acetylcysteine. For example, the analog of N-acetylcysteine can be an amino acid analog, i.e., a compound obtained by coupling N-acetylcysteine with an amino acid by forming ester, amide, and/or anhydride bond(s) between the amino acid and N-acetylcysteine. Any amino acid known to one skilled in the art can be used to make the amino acid analog. Examples of the analog include, but are not limited to the dimer of N-acetylcysteine, i.e., DiNAC, which is a disulfide molecule; N-acetylcysteine L-lysine, i.e., Nacystelyn or NAL; Carbocisteine; glutathione; S-nitroso-N-acetylcysteine; S-nitrosothiol-N-acetylcysteine; S-allyl-cysteine; S-alkyl-cysteine; N-acetyl-S-farnesyl-cysteine; N-acetyl-L-arginine-NAC; N-acetyl-L-lysine-NAC; N-acetyl-L-histidine-NAC; N-acetyl-L-ornithine-NAC; thioester of NAC with salicylic acid; 2'4'-difluoro-4-hydroxy-(1,1'-diphenyl)-3-carboxylic derivatives of NAC; S-allymercapto-NAC (ASSNaC); N,N-diacetyl-L-cystine; N—S-diacyl-cysteine; N-acetylcysteine conjugate of phenethyl isothiocyanate (PEITC-NAC); S-carboxylmethyl-L-cysteine; derivatives of reacting a reactive derivative of p-isobutylphenylpropionic acid and NAC (e.g., an amide); paraisobutyl NAC; and a combination thereof. The term "analog" includes the analog and its salts, solvates, and prodrugs.

"Salts" refers to a derivative of N-acetylcysteine, wherein N-acetylcysteine is modified by making acid or base addition salts thereof. The salt includes a salt of N-acetylcysteine, a salt of a prodrug of N-acetylcysteine, a salt of a solvate of N-acetylcysteine, and a salt of an analog of N-acetylcysteine. Examples of pharmaceutically acceptable salts include, but are not limited to, mineral or organic acid addition salts of basic residues such as amines; metal ion or organic base addition salts of acidic residues; and the like, or a combination comprising one or more of the foregoing salts. Examples of the metal ion include an alkali metal ion, an alkaline earth ion, and an aluminum ion. The pharmaceutically acceptable salts include salts and the quaternary ammonium salts of N-acetylcysteine. For example, acid salts include those derived from inorganic acids such as hydrochloric, hydrobromic, sulfuric, sulfamic, phosphoric, nitric and the like; other acceptable inorganic salts include metal salts such as sodium salt, potassium salt, cesium salt, and the like; and alkaline earth metal salts, such as calcium salt, magnesium salt, and the like, or a combination comprising one or more of the foregoing salts. Pharmaceutically acceptable organic salts includes salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, bile acids, and the like; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, asparginate, glutamate, and the like; or a combination comprising one or more of the foregoing salts. In some specific embodiments, the salts of N-acetylcysteine include sodium N-acetylcysteine and calcium N-acetylcysteine.

"Solvate" means a complex formed by solvation (the combination of solvent molecules with molecules or ions of N-acetylcysteine), or an aggregate that consists of a solute ion or molecule (N-acetylcysteine) with one or more solvent molecules. When water is the solvent, the corresponding solvate is "hydrate". The solvate includes a solvate of N-acetylcysteine, a solvate of a prodrug of N-acetylcysteine, a solvate of a salt of N-acetylcysteine, and a solvate of an analog of N-acetylcysteine.

"Prodrug" refers to a precursor of N-acetylcysteine wherein the precursor itself may or may not be pharmaceutically active but, upon administration, will be converted, either metabolically, for example hydrolyzed or oxidized, or otherwise, into N-acetylcysteine. For example, after being absorbed, the prodrug can be converted to the active compound (N-acetylcysteine) by naturally occurring serum enzyme. Typical examples of prodrugs include compounds that have biologically labile protecting groups on a functional moiety of N-acetylcysteine, such as the thiol and/or the carboxylic acid. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. For example, the prodrug includes an ester, an amide, an anhydride, or a thioether form of N-acetylcysteine.

In one embodiment of the present composition, the IR and/or SR component(s) comprises a prodrug of N-acetylcysteine. Preferably, the prodrug is less polar than N-acetylcysteine and is absorbable in the lower gastrointestinal (GI) tract of a mammal. The decreased polarity can improve absorption in the lower GI tract. The lower GI tract includes, but is not limited to the small intestine (duodenum, jejunum, and ileum) and large intestine (cecum, colon, and rectum). The polarity of the prodrug may be measured by any method known to one skilled in the art. In one embodiment, the polarity of the prodrug is measured by a partition coefficient, such as log P, which can be calculated or experimental and refers to the logarithm of the ratio of the concentration of the un-ionized solute, i.e., the prodrug of N-acetylcysteine, in the solvents, such as octanol-water. In one embodiment of the present invention, the prodrug has a log P value of 3.5, 3.6, 3.7, 3.8, 3.9, 4.0, 4.1, 4.2, 4.3, 4.4, 4.5, or higher.

In one embodiment of the present invention, the prodrug comprises a hydrophobic moiety. The hydrophobic moiety can be any organic radical which imparts non-polarity to the prodrug. For example, the hydrophobic moiety can be a hydrocarbon radical optionally substituted by one or more functional groups containing one or more heteroatoms. In one specific embodiment, the prodrug is an ester, amide, or anhydride of N-acetylcysteine having structures as shown in Scheme 2.

Scheme 2:

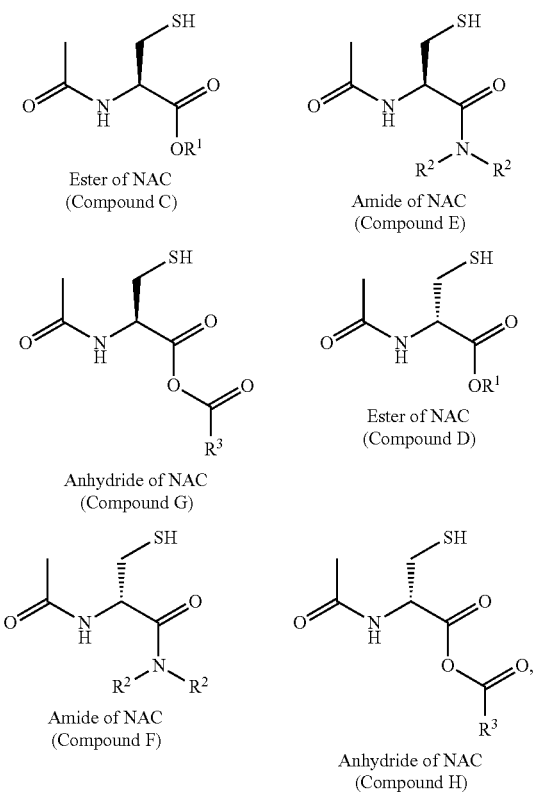

wherein:

$R^1$ and $R^3$ are independently alkyl, substituted alkyl, alkenyl, substituted alkenyl, aryl, substituted aryl, heteroaryl, or substituted heteroaryl; and each $R^2$ are independently hydrogen, alkyl, substituted alkyl, alkenyl, substituted alkenyl, aryl, substituted aryl, heteroaryl, or substituted heteroaryl.

In one embodiment, the anhydride of NAC is an anhydride of two NAC, i.e., an anhydride dimer of NAC as shown below:

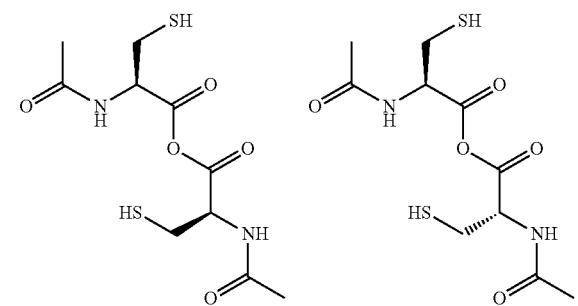

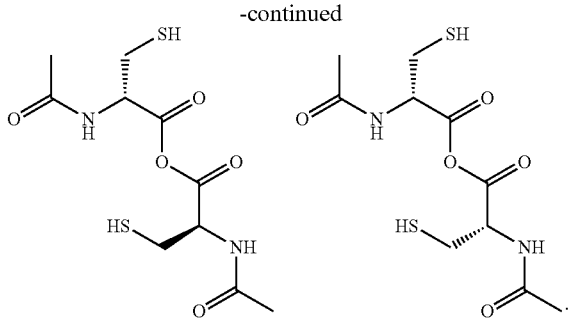

The term "alkyl", by itself or as part of other substituents, refers to a saturated straight, branched, or cyclic, primary, secondary, or tertiary hydrocarbon, including but not limited to groups with $C_1$ to $C_{10}$. The term "alkyl" includes "lower alkyl". The term "lower alkyl" refers to a saturated straight, branched, or cyclic, primary, secondary, or tertiary hydrocarbon, including groups with $C_1$ to $C_4$, and if appropriate a cyclic alkyl group (for example cyclopropyl). The term "alkyl" also includes "cycloalkyl", "heteroalkyl", "heterocycloalkyl", "arylalkyl", and "heterarylalkyl" as defined herein below.

Illustrative examples of alkyl groups are methyl, ethyl, propyl, isopropyl, cyclopropyl, butyl, sec-butyl, isobutyl, tert-butyl, cyclobutyl, 1-methylbutyl, 1,1-dimethylpropyl, pentyl, cyclopentyl, isopentyl, neopentyl, cyclopentyl, hexyl, isohexyl, and cyclohexyl. Unless otherwise specified, the alkyl group can be unsubstituted or substituted with one or more moieties selected from the group consisting of alkyl, halo, haloalkyl, hydroxyl, carboxyl, acyl, acyloxy, amino, amido, carboxyl derivatives, alkylamino, dialkylamino, arylamino, alkoxy, aryloxy, nitro, cyano, thiol, imine, sulfonic acid, sulfate, sulfonyl, sulfanyl, sulfonyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphate, phosphonate, or any other viable functional group that does not inhibit the pharmacological activity of this compound, either unprotected, or protected as necessary, as known to those skilled in the art, for example, as taught in Greene, et al., *Protective Groups in Organic Synthesis*, John Wiley and Sons, Second Edition, 1991.

The terms "alkenyl", by itself or as part of other substituents, refer to alkyl moieties, including both substituted and unsubstituted forms wherein at least one saturated C—C bond is replaced by a double bond. Thus, $C_{2-6}$ alkenyl may be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl.

"Alkyl" or "alkenyl" includes both straight chain and branched groups. However, reference to an individual radical such as "propyl" embraces only that straight-chain radical, whereas a branched chain isomer such as "isopropyl" is specifically termed such.

The term "aryl", by themselves or as part of other substituents, as used herein and unless otherwise specified refers to any stable monocyclic, bicyclic, or tricyclic carbon ring of up to 8 members in each ring, wherein at least one ring is aromatic as defined by the Huckel 4n+2 rule, and especially phenyl, biphenyl, or naphthyl. The term includes both substituted and unsubstituted moieties. The aryl group can be substituted with any described moiety, including but not limited to one or more moieties selected from the group consisting of halogen (fluoro, chloro, bromo or iodo), hydroxyl, amino, azido, alkylamino, arylamino, alkoxy, aryloxy, nitro, cyano, sulfonic acid, sulfate, phosphonic acid, phosphate, or phosphonate, either protected or unprotected as necessary, as known to those skilled in the art, for example, as taught in Greene et al., *Protective Groups in Organic Synthesis*, John Wiley & Sons, $3^{rd}$ Ed., 1999.

The term "alkaryl" or "alkylaryl" refers to an alkyl group with an aryl substituent or an alkyl group linked to the molecule through an aryl group as defined herein. The term "aralkyl" or "arylalkyl" refers to an aryl group substituted with an alkyl substituent or linked to the molecule through an alkyl group as defined above.

The term "cycloalkyl", by themselves or as part of other substituents, includes a ring of $C_{3-8}$, including but not limited to cyclopropyl, cyclobutyl, cyclopentyl, cyclohexyl, cycloheptyl and cyclooctyl.

The term "heteroalkyl", by themselves or as part of other substituents, refer to an alkyl group in which one or more of the carbon atoms (and optionally any associated hydrogen atoms), are each, independently of one another, replaced with the same or different heteroatoms or heteroatomic groups. The heteroatoms or heteroatomic groups may be placed at any interior position of the alkyl group.

The term "heteratom" includes an atom other than carbon or hydrogen in the structure of a heterocyclic compound, nonlimiting examples of which are nitrogen, oxygen, sulfur, phosphorus or boron.

The term "cycloheteroalkyl" by itself or as part of another substituent, refers to a cyclic alkyl radical in which one or more carbon atoms (and optionally any associated hydrogen atoms) are independently replaced with the same or different heteroatom.

The term "heterocycle", "heterocyclyl", or "heterocyclic" as used herein includes non-aromatic ring systems having four to fourteen members, preferably five to ten, in which one or more ring carbons, preferably one to four, are each replaced by a heteroatom. Heterocycle includes, but is not limited to, cycloheteroalkyl. Examples of heterocyclic rings include 3-1H-benzimidazol-2-one, (1-substituted)-2-oxo-benzimidazol-3-yl, 2-tetrahydro-furanyl, 3-tetrahydrofuranyl, 2-tetrahydropyranyl, 3-tetrahydropyranyl, 4-tetra-hydropyranyl, [1,3]-dioxalanyl, [1,3]-dithiolanyl, [1,3]-dioxanyl, 2-tetrahydro-thiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrrolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-phthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenanthridinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally substituted.

The term "heteroaryl", used alone or as part of a larger moiety as in "heteroaralkyl" or "heteroarylalkoxy", refers to heteroaromatic ring groups having five to fourteen members. Examples of heteroaryl rings include 2-furanyl, 3-furanyl, 3-furazanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 2-pyrazolyl, 3-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, and benzoisoxazolyl. Also included within the scope of the term "heteroaryl", as it is used herein, is a group in which a heteroatomic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" also refers to rings that are optionally substituted. The term "heteroaryl" may be used interchangeably with the term "heteroaryl ring" or the term "heteroaromatic".

Certain specific compounds of the present invention are defined as follows:

N-acetyl-L cysteine is Compound A;
N-acetyl-D-cysteine is Compound B;
The ester prodrugs of N-acetyl-L-cysteine are Compounds C, where the prodrugs have the general structure as shown in Scheme 2, wherein the $R^1$ group can be methyl (C1), ethyl (C2), propyl (C3), butyl (C4), pentyl (C5), or hexyl (C6) group;
The ester prodrugs of N-acetyl-D-cysteine are Compounds D, where the prodrugs have the general structure as shown in Scheme 2, wherein the $R^1$ group can be methyl (D1), ethyl (D2), propyl (D3), butyl (D4), pentyl (D5), or hexyl (D6) group;
The amide prodrugs of N-acetyl-L-cysteine are Compounds E, where the prodrug has the general chemical structure as shown in Scheme 2, wherein one of $R^2$ is hydrogen, and the other $R^2$ independently can be methyl (E1), ethyl (E2), propyl (E3) butyl (E4), pentyl (E5) or hexyl (E6);
The amide prodrugs of N-acetyl-D-cysteine are Compounds F, where the prodrug has the general chemical structure as shown in Scheme 2, wherein one of $R^2$ is hydrogen, and the other $R^2$ independently can be methyl (F1), ethyl (F2), propyl (F3) butyl (F4), pentyl (F5) or hexyl (F6);
The anhydride prodrugs of N-acetyl-L-cysteine is Compound G, where the prodrug has the general chemical structure as shown in Scheme 2;
The anhydride prodrug of N-acetyl-D-cysteine is Compound H where the prodrugs have the chemical structure as shown in Scheme 2;
The dimer of N-acetylcysteine, DiNAC is Compound I;
N-acetylcysteine L-lysinate (Nacystelyn) is Compound I; and
Carbocisteine is Compound K.

In another embodiment, the present invention provides a sustained-release composition comprising a modified N-acetylcysteine, or a salt and/or solvate thereof; and a release-rate controlling polymer. The modified N-acetylcysteine, or a salt and/or solvate thereof, is less polar than N-acetylcysteine, and thereby is more absorbable in the lower GI tract than N-acetylcysteine is. By "modified N-acetylcysteine", it is meant a compound that is structurally related to and chemically derivable from N-acetylcysteine. For example, the modified N-acetylcysteine can be made from N-acetylcysteine by adding one or more hydrophobic moieties to N-acetylcystein. Examples of the modified N-acetylcystein include, but are not limited to the prodrugs and analogs of N-acetylcystein as described herein.

The sustained-release composition may be formulated to various delivery systems including matrix delivery system, osmotic delivery system, or multiparticulates delivery system. For example, the release rate controlling polymer may be mixed with the modified N-acetylcysteine, or a salt and/or solvate thereof, to form a Matrix; or alternatively, the release rate controlling polymer is disposed over the modified N-acetylcysteine, or a salt and/or solvate thereof, to form a coating. The release rate controlling polymer is the same as described hereinabove. The release of the active agent by the sustained-release composition is extended for longer than it would be in an immediate-release composition, e.g., at least over several hours. The sustained-release composition may further optionally comprise one or more pharmaceutically acceptable excipient as described herein.

The modified N-acetylcystein of the present invention can be prepared by any method known to one skilled in the art. For example, methods for preparing esters, amides, and anhydrides from a carboxylic acid are well known in the field of organic chemistry. Thus, the ester, amide, and anhydride prodrugs of NAC can be prepared according to these known methods. Specific methods and procedures can be found in Francis A. Carey and Richard J. Sundberg, "Advanced Organic Chemistry, Part B: Reactions and Synthesis", fifth edition, Springer Science+Business Media, LLC, 2007.

Controlled Release Compositions

In one embodiment, the present invention provides a composition comprising a sustained release (SR) component. The SR component comprises N-acetylcysteine, or a salt, solvate, prodrug, and/or analog thereof. In one embodiment, the composition is mono-modal and provides a sustained release profile. Upon oral administration, the composition provides a therapeutically effective plasma concentration of N-acetylcysteine over about 2 to about 24 hours following the administration. In another embodiment, the composition can provide a therapeutically effective plasma concentration of N-acetylcysteine about 2.5 hours after the administration. In another embodiment, the composition can provide a therapeutically effective plasma concentration of N-acetylcysteine about 3 hours after the administration. In another embodiment, the composition provides a therapeutically effective plasma concentration of N-acetylcysteine until about 20 hours following the administration. In another embodiment, the composition provides a therapeutically effective plasma concentration of N-acetylcysteine until about 16 hours after the administration. In another embodiment, the composition provides a therapeutically effective plasma concentration of N-acetylcysteine until about 12 hours after the administration. In another embodiment, the composition provides a therapeutically effective plasma concentration of N-acetylcysteine until about 8 hours after the administration.

In one embodiment of the composition comprising a SR component, the SR component comprises N-acetylcysteine, or a salt and/or solvate thereof. Preferably, the SR component or the composition does not contain a rheology modifying polymer. For example, the rheology modifying polymer can be a granulated, rheology modifying, release-controlling, slightly cross-linked polymer of acrylic acid, methacrylic acid, or an analog thereof. Examples of the rheology modifying polymer are described in details in U.S. Pat. No. 6,623,754, the disclosures of which are herein incorporated by reference in its entirety. In another embodiment of the composition comprising a SR component, the SR component comprises N-acetylcysteine, or a prodrug and/or analog thereof, wherein the SR component or the composition may or may not further comprise a rhenology modifying polymer.

In another embodiment, the present invention provides a composition comprising an immediate release (IR) component and a sustained release (SR) component. The IR component comprises N-acetylcysteine, or a salt, solvate, prodrug, and/or analog thereof; and the SR component comprises N-acetylcysteine, or a salt, solvate, prodrug, and/or analog thereof. The composition provides a bi-modal release profile. That is, upon oral administration, the IR component readily release N-acetylcysteine, or a salt, solvate, prodrug, and/or analog thereof and thereby provides a therapeutically effective plasma concentration of N-acetylcysteine, for instance, within about 20 to about 40 minutes and maintains the therapeutically effective plasma concentration of N-acetylcysteine for about 2 to 4 hours. In one embodiment, the IR component provides a therapeutically effective plasma concentration of N-acetylcysteine over about 30 minutes to about 3 hours. As N-acetylcysteine released by the IR component is absorbed and metabolized, the SR component starts to release N-acetylcysteine and provides a sustained release profile as described above. That is, the SR component can provides a therapeutically effective plasma concentration of N-acetylcysteine for about 8, 12, 16, 20, up to, or more than 24 hours. Thus, the bi-modal composition, upon administration provides a therapeutically effective plasma concentration of N-acetylcysteine over, for instances, about 20 minutes to about 24 hours following the administration. In another embodiment, the composition provides a therapeutically effective plasma concentration of N-acetylcysteine over about 30 minutes to about 24 hours following the administration. In another embodiment, the composition provides a therapeutically effective plasma concentration of N-acetylcysteine over about 40 minutes to about 24 hours following the administration.

"Therapeutically effective", as used herein, means the amount of N-acetylcysteine, when administered to a patient for treating a disease, condition, and/or symptom, is sufficient to effect such treatment for the disease, condition, and/or symptom. The therapeutically effective amount, such as the plasma concentration, will vary depending on the compound, the disease and its severity and the age, weight, etc., of the patient to be treated. As used herein, the terms "mammal" and "patient" are used interchangeably and refer to a human or domestic animal (including both farm animals and companion animals).

Various mono- or bi-modal delivery systems comprising the composition of the present invention may be formulated to provide a release profile as described herein. For example, the present composition can be formulated as a matrix, osmotic, and/or multiparticulate delivery system. Each of the delivery systems can be mono- or bi-modal. The composition may be provided in any dosage form suitable for sustained release of a drug. A "dosage form" means a unit of administration of N-acetylcysteine, or a salt, solvate, prodrug, and/or analog thereof. Examples of dosage forms include tablets, mini-tablets, capsules, microcapsules, injections, suspensions, liquids, emulsions, creams, ointments, suppositories, inhalable forms, transdermal forms, and the like. Preferred dosage form of the present invention is oral dosage form. An "oral dosage form" means a unit dosage form for oral administration.

In one embodiment, the composition comprises an SR component, wherein the SR component comprises a matrix. The matrix comprises N-acetylcysteine, or a salt, solvate, prodrug, and/or analog thereof; and a release rate controlling polymer. The matrix optionally further comprises one or more pharmaceutically acceptable excipients. As used herein, the term "matrix" denotes a homogeneous solid mixture composed of evenly dispersed ingredients throughout. The composition, in a whole or a portion, may be in form of a matrix. For example, the composition may be composed of a matrix core and a coating over the matrix core; or alternatively, the composition may be composed of two matrices as two portions of the composition. In one embodiment, the matrix as described herein is further coated with an enteric coating.

By "release rate controlling polymer", it is meant any polymer which can control the release of N-acetylcysteine, or a salt, solvate, prodrug, and/or analog thereof, from the composition in such a way to obtain the desired release profile as described herein. In one embodiment, the release rate controlling polymer is a hydrophilic polymer. The term "hydrophilic polymer" refers to a polymer having a strong affinity for water and tending to dissolve in, mix with, or be wetted by water. Examples of the hydrophilic polymer include, but are not limited to polyethylene oxide, hydroxypropyl cellulose, hydroxypropyl methyl cellulose, hydroxyethyl cellulose, sodium carboxymethylcellulose, calcium carboxymethyl cellulose, methyl cellulose, polyacrylic acid, maltodextrin, pregelatinized starch, guar gum, sodium alginate, polyvinyl alcohol, chitosan, locust bean gum, amylase, any other water-swelling polymer, and a combination thereof.

In another embodiment, the composition comprises both an IR and SR components, wherein the SR component comprises a matrix as described herein. The IR component comprises N-acetylcysteine, or a salt, solvate, prodrug, and/or analog thereof, optionally in a matrix form. The IR component optionally further comprises one or more pharmaceutically acceptable excipients.

In one embodiment, the composition is formulated to an osmotic delivery system. For example, the composition comprises a release rate controlling membrane disposed over a pull layer and an osmotic push layer, wherein the pull layer comprises N-acetylcysteine, or a salt, solvate, prodrug, and/or analog thereof, and the release rate controlling membrane has an orifice immediately adjacent to the pull layer. The pull layer further optionally comprises a release rate controlling polymer and/or a pharmaceutically acceptable excipient. The release rate controlling membrane is a semipermeable wall that surrounds the pull layer and the osmotic push layer. The wall is permeable to the passage of fluid and has an orifice which allows passage of N-acetylcysteine, or a salt, solvate, prodrug, and/or analog thereof, from inside of the wall to outside. Upon being exposed to biological or other fluids, the semipermeable wall allows permeation of the fluids through the wall causing expansion of the osmotic push layer, and consequently the osmotic push layer pushes the pull layer through the orifice. The release rate of N-acetylcysteine, or a salt, solvate, prodrug, and/or analog thereof, is determined by the permeability of the wall and the osmotic pressure gradient across the wall.

There may be one or more pull layers and/or one or more osmotic push layers encapsulated by the release rate controlling membrane. In one embodiment, the release rate controlling membrane encapsulates one pull layer and one osmotic push layer, wherein the pull layer comprises N-acetylcysteine, or a salt, solvate, prodrug, and/or analog thereof, and optionally a release rate controlling polymer. That is, the pull layer may comprise either the IR component or the SR component. In another embodiment, the release rate controlling membrane encapsulates a first pull layer comprising the IR component, a second pull layer comprising the SR component, and an osmotic push layer; wherein the release rate controlling membrane has an orifice immediately adjacent to the first pull layer. Both the IR and SR components comprise N-acetylcysteine, or a salt, solvate, prodrug, and/or analog thereof, and further optionally independently comprise a pharmaceutically acceptable excipient. In one embodiment, the SR component comprises a matrix which contains N-acetylcysteine, or a salt, solvate, prodrug, and/or analog thereof; and a release rate controlling polymer. The release rate controlling polymer in the osmotic delivery system is the same as described above.

The release rate controlling membrane can be made of any material that is non-erodable, nontoxic, and insoluble in fluids, and can form a semipermeable wall as described herein. Examples of materials for forming the wall include, but are not limited to cellulose esters, cellulose ethers, cellulose ester-ethers, and combinations thereof. Additional examples include cellulose acylate, cellulose diacylate, cellulose triacylate, cellulose acetate, cellulose diacetate, cellulose triacetate, mono-, di- and tricellulose alkanylates, mono-, di- and tricellulose aroylates, and the like. Exemplary polymers include cellulose acetate having a D.S. up to 1 and acetyl content up to 21%; cellulose acetate having an acetyl content of 32 to 39.8%: cellulose diacetate having a D.S. of 1 of 2 and an acetyl content of 21 to 35%; cellulose triacetate having a D.S. of 2 to 3 and an acetyl content of to 44.8%; and the like. More specific cellulosic polymers include cellulose propionate having a D.S. of 1.8 and a propionyl content of 39.2 to 45% and a hydroxyl content of 2.8 to 5.4%; cellulose acetate-butyrate having a D.S. of 1.8, and acetyl content of 13 to 15% and a butyryl content of 34 to 39%; cellulose acetate butyrate having an acetyl content of 2 to 29%, a butyryl content of 17 to 53% and a hydroxyl content of 0.5 to 4.7%; cellulose triacylates having a D.S. of 2.9 to 3 such as cellulose trivalerate, cellulose trilaurate, cellulose tripalmitate, cellulose trisuccinate, and cellulose trioclanoate; cellulose diacylates having a D.S. of 2.2 to 2.6 such as cellulose disuccinate, cellulose dipalmitate, cellulose dioclanoate, cellulose dipentale, and the like.

In one embodiment, the osmotic push layer comprises an osmopolymer. The osmopolymers are typically hydrophilic polymers and interact with water and aqueous biological fluids and swell or expand to push a drug composition through the orifice. The osmopolymers exhibit the ability to swell in water and retain a significant portion of the imbibed water within the polymer structure. The osmopolymers may swell or expand to a very high degree. The osmopolymers can be noncross-linked or cross-linked. The swellable, hydrophilic polymers may be lightly cross-linked, such as cross-links being formed by covalent or ionic bonds. The osmopolymers can be of plant, animal or synthetic origin. Hydrophilic polymers suitable for the present purpose include, but are not limited to poly(hydroxyalkylmethacrylate) having a molecular weight of from 30,000 to 5,000,000; polyvinylpyrrolidone) having molecular weight of from 10,000 to 360,000; anionic and cationic hydrogels; polyelectrolyte complexes, poly(vinyl alcohol) having a low acetate residual, cross-linked with glyoxal, formaldehyde, or glutaraldehyde and having a degree of polymerization from 200 to 30,000; a mixture of methyl cellulose, cross-linked agar and carboxymethyl cellulose; a water insoluble, water swellable copolymer reduced by forming a dispersion of finely divided copolymer of maleic anhydride with styrene, ethylene, propylene, butylene or isobutylene cross-linked with from 0.00001 to about 0.5 moles of polyunsaturated cross-linking agent per mole of maleic anhydride in the copolymer, water swellable polymers of N-vinyl lactams, and the like. Other osmopolymers include hydrogel polymers, such as Carbopol (acrylic acid-based polymers crosslinked with polyalkylene polyethers) and the sodium salt thereof; acidic carboxy polymers generally having a molecular weight of 450,000 to 4,000,000 and their metal salts; Polyox; polyethylene oxide polymers having a molecular weight of 100,000 to 7,500,000.

In one embodiment, the pull layer further comprises an osmagent, also known as osmotically effective solutes. The osmagent can be any compound, inorganic or organic, that exhibit an osmotic pressure gradient across an external fluid across the semipermeable wall. In one embodiment, the osmagent is a solid. Examples of the osmagent include, but are not limited to a salt, oxide, carbohydrate, acid, ester, magnesium sulfate, magnesium chloride, sodium chloride, potassium chloride, lithium chloride, potassium sulfate, sodium sulfate, lithium sulfate, lithium phosphate, sodium phosphate, potassium phosphate, potassium acid phosphate, calcium lactate, mannitol, urea, inositol, magnesium succinate, tartaric acid, carbohydrates such as raffinose, sucrose, glucose, lactose monohydrate, and a blend of fructose glucose.

In one embodiment, the composition of the present invention is formulated to a multiparticulate delivery system. Certain examples of the multiparticulate delivery system and the manufacturing thereof are described in detail in Lu, Int. J. Pharm., 1994, 112, pages 117-124, the content of which is herein incorporated by reference in its entirety. In one embodiment, the SR component of the composition comprises one or more particles and each of the particles comprises an active core comprising N-acetylcysteine, or a salt, solvate, prodrug, and/or analog thereof; and a release rate controlling polymer disposed over the core. In another embodiment, the SR component of the composition comprises one or more particles and each of the particles comprises an inert core, an active layer comprising N-acetylcysteine, or a salt, solvate, prodrug, and/or analog thereof disposed over the inert core, and a release rate controlling polymer disposed over the active layer. In one embodiment, the present composition comprises both the IR and SR components and each of the IR and SR components comprises one or more particles. In one embodiment, the IR component comprises an inert core, and a cotaing disposed over the inert core, wherein the coating comprises N-acetylcysteine, or a salt, solvate, prodrug, and/or derivatives thereof. In yet another embodiment, the composition comprises one or more particles and each of the particles comprises the IR and SR components, wherein the IR component forms a layer encapsulating the SR component and optionally there are one or more additional layers between the IR component and the SR component. Any of the active core, the inert core, the active layer, the coating, or the coating formed by the release rate controlling polymer disposed over the active layer may optionally further comprise a pharmaceutically acceptable excipient.

The term "particle" denotes a small discrete mass of solid, semi-solid, or liquid matter that remains individually dispersed in the composition. The particles can be in any shape including spherical, round, elliptical, square, rectangular, triangular, polygonal, or irregular shape. Depending on the shape, the process of preparation, and the intended use of the particle, it may be referred to as pellet, seed, bead, spheroid, or granule. For example, a granule is a particle obtained through a granulation process; a bead is a round-shaped particle.

In one embodiment of the multiparticulate delivery system, the release rate controlling polymer comprises a film-forming, water insoluble polymer in combination with a film-forming, water soluble polymer. The ratio between the water insoluble polymer and the water soluble polymer can be adjusted depending on the intended drug release profile. In one embodiment, the release rate controlling polymer comprises a major proportion of a pharmaceutically acceptable film-forming, water insoluble polymer, and a minor proportion of a pharmaceutically acceptable film-forming, water soluble polymer. A coating can be formed by disposing the release rate controlling polymer over the core or the active layer, and the thickness of the coating can be adjusted to permit the release of N-acetylcysteine, or a salt, solvate, prodrug, and/or derivatives thereof with an intended profile.

Examples of the film-forming, water insoluble polymer include, but are not limited to ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene oxide), poly(ethylene terephthalate), poly(vinyl isobutyl ether), poly(vinyl acetate), poly(vinyl chloride) or polyurethane, or any other water insoluble polymer, or mixtures thereof.

Examples of the film-forming, water soluble polymer include, but are not limited to polyvinyl alcohol, polyvinylpyrrolidone, methyl cellulose, hydroxypropyl cellulose, hydroxypropylmethyl cellulose and polyethylene glycol, Pluronic F108, Pluronic F127, Pluronic F68 or mixtures thereof "Pharmaceutically acceptable" refers to being suitable for use in contact with the tissues of humans and animals without undue toxicity, irritation, allergic response, and the like, commensurate with a reasonable benefit/risk ratio, and effective for their intended use within the scope of sound medical judgment. "Excipient" denotes a diluent, adjuvant, vehicle or carrier with which N-acetylcysteine, or a salt, solvate, prodrug, and/or analog thereof, is administered. Examples of the pharmaceutically acceptable excipient include, are not limited to a filler (or diluent), a binder, a disintegrant, a lubricant, or a combination thereof.

Fillers may be one or more compounds which are capable of providing compactability and good flow. Examples of fillers include microcrystalline cellulose, starch, lactose, sucrose, glucose, mannitol, maltodextrin, sorbitol, dextrose, silicic acid, dibasic calcium phosphate, or a combination comprising at least one of the foregoing fillers. Exemplary lactose forms include lactose monohydrate, NF (Fast Flo), lactose spray-dried monohydrate, and lactose anhydrous. Exemplary microcrystalline celluloses (MCC) include, for example, AVICEL® PH101 and AVICEL® PH102, which are commercially available from FMC Biopolymer, Philadelphia, Pa.

Binders may be used to impart cohesive qualities to a formulation, for example, a tablet formulation, and thus ensure that the tablet remains intact after compaction. Examples of binders include starches (for example, Starch 1500® or pregelatinized starch), alignates, gelatin, carboxymethylcellulose, sugars (for example, sucrose, glucose, dextrose, and maltodextrin), polyethylene glycol, waxes, natural and synthetic gums, polyvinylpyrrolidone, and cellulosic polymers (for example, microcrystalline cellulose, hydroxypropyl cellulose, hydroxypropyl methylcellulose, methyl cellulose, and hydroxyethyl cellulose) and combinations comprising one or more of the foregoing binders.

Disintegrants are used to facilitate disintegration or "breakup" of a composition, for example, a tablet, after administration. Examples of disintegrants include sodium starch glycolate, sodium croscarmellose (cross-linked carboxy methyl cellulose), crosslinked polyvinylpyrrolidone (PVP-XL), anhydrous calcium hydrogen phosphate, agar-agar, potato or tapioca starch, alginic acid, or a combination comprising one or more of the foregoing disintegrants.

A lubricant may be added to the composition for a minimum period of time to obtain good dispersal. Examples of lubricants include magnesium stearate, calcium stearate, zinc stearate, stearic acid, talc, glyceryl behenate, polyethylene glycol, polyethylene glycol, polyethylene oxide, sodium lauryl sulfate, magnesium lauryl sulfate, sodium oleate, sodium stearyl fumarate, DL-leucine, colloidal silica, or a combination comprising one or more of the foregoing lubricants.

If desired, the composition may optionally comprise small amounts of nontoxic auxiliary substances such as wetting or emulsifying agents, or pH buffering agents, for example, sodium acetate, sorbitan monolaurate, triethanolamine sodium acetate, triethanolamine oleate, sodium lauryl sulfate, dioctyl sodium sulfosuccinate, and polyoxyethylene sorbitan fatty acid esters.

The ratio among the active ingredient (N-acetylcysteine, or a salt, solvate, prodrug, and/or analog thereof), the release rate controlling polymer, osmopolymer, osmagent, and other pharmaceutically acceptable excipients can be adjusted according to the intended release profile and therapeutic objective. In one embodiment, the present composition comprises from about 10 to about 90 wt. % of the active ingredient, with the range from about 20 to about 80 wt. % more preferred, and with the range from about 30 to about 70 wt. % most preferred. In one specific embodiment, the composition comprises about 60 wt. % of the active ingredient. In other embodiments, the composition comprises about 10 wt. %, about 20 wt. %, about 30 wt. %, about 40 wt. %, about 50 wt. %, about 60 wt. %, about 70 wt. %, about 80 wt. %, or about 90 wt. % of the active ingredient, inclusive of all ranges and subranges therebetween.

Therapeutic Usage

The present invention also provides a method of reducing a vascular inflammatory marker or mediator in a mammal. The method comprises orally administering to the mammal the composition of the present invention. "Vascular inflammatory marker or mediator" means a biological substance that relates to or that is used to identify vascular inflammatory. Examples of the vascular inflammatory marker or mediator include, but are not limited to C-reactive protein (CRP); lipoprotein-associated phospholipase A2 (LP-PLA2); lipoprotein Lp(a); myeloperoxidase (MPO); macrophage chemotactic protein 1 (MCP-1); interleukins (IL), such as IL-1, 6, 8, 10; oxidized low-density lipoprotein (oxidized LDL), adiponectin, matrix metaloproteinases (MMP), such as MMP-9, 1, 2; CD40; homocysteine; cardiovascular risk factor (CVRF); plasminogen activator inhibitor (PAI-1); prostaglandin (PG); tissue polypeptide antigen (TPA); von Willebrand factor (vWF); platelet aggregation; fibrinogen; Factor VII; Factor VIII; tissue factor; phosphoglucose (PGI1); endothelin; metaloproteinases; Lipoxegenase; angiotensin; and a combination thereof.

In one embodiment, the present invention provides a method of reducing systemic, organ-specific, and/or vascular inflammation in a mammal. The method comprises orally administering to the mammal the composition of the present invention.

In one embodiment, the present invention provides a method of treating a disease, condition, or symptom associated with systemic and/or vascular inflammation in a mammal. The term "treating", as used herein, means preventing, relieving, ameliorating, and/or curing an illness including a disease, condition, and/or symptom as well as reducing the frequency of occurrence of adverse health event (e.g., acute coronary events). The term "associated with systemic and/or vascular inflammation" denotes a disease, condition, and/or symptom that accompanies or is connected with systemic and/or vascular inflammation. Such a disease, condition, and/or symptom may directly or indirectly cause or be caused by systemic and/or vascular inflammation. The method comprises orally administering to the mammal the composition or the present invention. In one embodiment, the disease, condition, or symptom is related to the circulatory system of the mammal. Examples of the disease, condition, or symptom include, but are not limited to liver inflammation; pancreatitis; myocardial hyperthrophy; pulmonary fibrosis, such as pulmonary fibrosis related to radiation damage; endotoxic shock; uveitis; dementia including Alzheimer's dementia and AIDS dementia; Parkinson's disease; brain toxicity; kidney damage from radiographic dyes; cancer drugs toxicity, such as the toxicity of methotrexate (MTX); AIDS; atherosclerosis, arthritis, diabetes, colitis, multiple sclerosis, acute coronary syndrome, and acute myocardial infarction. The liver inflammation may be related to or caused by a disease, such as acute or chronic hepatitis, ischemic hepatitis, viral hepatitis, autoimmune diseasees, metabolic diseases (e.g., Wilson's disease), non-alcoholic steatohepatitis, primary biliary cirrhosis, and primary sclerosing cholangitis; a body condition, such as pregancy; and/or the use of certain substance, such as alcohol, toxins, and drugs including acetaminophen (TYLENOL), amoxycillin, antituberculosis drugs, minocycline, ibuprofen, and other drugs having liver toxicity. In one specific embodiment, the method comprises orally administering to the mammal the composition of the present invention for treating liver inflammation caused by acetaminophen.

Manufacturing Process

It has been known that NAC may degrade via hydrolysis during the manufacturing process, especially in a granulation process employing an aqueous solution. U.S. Pat. No. 6,623,754 describes a direct compression process to avoid NAC hydrolysis. However, this process limits the selection of excipients and requires large size drug particles. Therefore, the present invention provides an alternative process to manufacture the controlled-release composition comprising N-acetylcysteine, or a salt, solvate, prodrug, and/or analog thereof, with minimal NAC degradation. The process does not utilize a solvent, particularly water. In one embodiment, the process for making granules comprising N-acetylcysteine, or a salt, solvate, prodrug, and/or analog thereof, comprises the steps of applying forces to loose solids comprising N-acetylcysteine, or a salt, solvate, prodrug, and/or analog thereof, thereby obtaining a solid sheet; and reducing the size of the solid sheet, thereby obtaining granules. By "loose solids", it is meant solids that are not pressed, compacted, or otherwise processed to have a fixed shape to some extent. In one embodiment, the applying step is carried out by pressing the loose solids between two counter rotating rolls. The granules further optionally comprise one or more pharmaceutically acceptable excipients. In one embodiment of the process, a roller compactor forces powdery and fine crystalline excipients and NAC or it prodrug between two counter rotating rolls and presses them into a solid compact or sheet, so called flakes. Then, these flakes are reduced to desired particle size for further process such as compression to tablets. Since this granulation method does not involve any solvents, especially water, the potential for drug degradation is eliminated.

Combination Therapy

In one embodiment, a composition or formulation comprising N-acetylcysteine, or a salt, solvate, prodrug, and/or analog thereof, may be used in combination with at least one additional active agent. The additional active agent can be any compound, agent, molecule, composition, or medication that have biological activity or therapeutic effect. For example, the additional active agent may enhance the therapeutic effect of or generate synergistic effect with N-acetylcysteine, or a salt, solvate, prodrug, and/or analog thereof. Alternatively, the toxicity or side effect of the additional active agent may be reduced by N-acetylcysteine, or a salt, solvate, prodrug, and/or analog thereof. The additional active agent can be a small-molecule drug, biologics, herbal composition, or a treatment method, such as radiotherapy. In one embodiment, the additional active agent is a drug for treating cadiovascular and/or metabolism diseases. Preferably, the additional active agent is a statin. Examples of the statins include, but are not limited to atorvastatin, cerivastatin, fluvastatin, lovastatin, mevastatin, pitavastatin, pravastatin, rosuvastatin, simvastatin, and a combination thereof.

In one embodiment, the present invention provides a method of treating a disease, condition, or symptom associated with systemic and/or vascular inflammation in a mammal comprising co-administering to the mammal (a) N-acetylcysteine, or a salt, solvate, prodrug, and/or analog thereof; and (b) at least one additional active agent. The term "co-administration" or "coadministration" refers to administration of the above-mentioned components (a) and (b) together in a coordinated fashion. For example, the co-administration can be simultaneous administration, i.e., administration of (a) and (b) at the same time; sequential administration, i.e., administration of (a) and (b) in succession within a short period of time, such as within a couple of hours; separate administration, i.e., administration of (a) and (b) that is not simultaneous or sequential, but is according to a predetermined dosing regimen or schedule; or a combination thereof. Furthermore, the co-administration includes the administration of a single dosage form containing both (a) and (b); and two separate dosage forms containing (a) and (b), respectively.

The dosing amount of (a) and (b) needs to be a therapeutically effective amount and may vary for each patient depending on the individual patient's condition. The term "therapeutically effective amount", as used herein, denotes an amount that can produce one or more intended biological effects in a patient, such as preventing, ameliorating, relieving, improving, or remedying the disease, condition, and/or symptoms.

In one embodiment, the present invention provides a composition comprising (a) N-acetylcysteine, or a salt, solvate, prodrug, and/or analog thereof; and (b) at least one additional active agent. The component (a) may include a sustained release component comprising N-acetylcysteine, or a salt, solvate, prodrug, and/or analog thereof; and a release rate controlling polymer as described herein. The sustained release component can be formulated to any delivery system as described herein. The component (a) may further optionally include an immediate release component comprising N-acetylcysteine, or a salt, solvate, prodrug, and/or analog thereof. Furthermore, the composition may optionally contain one or more pharmaceutically acceptable excipient as described herein.

In one embodiment, the present invention provides a combination package comprising (a) at least one individual dose of N-acetylcysteine, or a salt, solvate, prodrug, and/or analog thereof; and (b) at least one individual dose of an additional active agent. The combination package may further optionally comprise an instruction document providing a protocol for co-administering (a) and (b). Each of the individual dose may be formulated to a pharmaceutical composition or a dosage form thereof. Component (b) may be included in either or both the SR or IR forms, layers, etc. or may be formulated as a separate dosage form, within or external to the NAC component.

In one embodiment, the present invention provides a method of distributing a therapeutic agent comprising distributing to a patient a predetermined amount of a first pharmaceutical composition comprising N-acetylcysteine, or a salt, solvate, prodrug, and/or analog thereof, in combination with a predetermined amount of a second pharmaceutical composition comprising at least one additional active agent. In one embodiment, the present invention provides a method of distributing a therapeutic agent comprising distributing to a patient a predetermined amount of a first pharmaceutical composition comprising at least one active agent, in combination with a predetermined amount of a second pharmaceutical composition comprising N-acetylcysteine, or a salt, solvate, prodrug, and/or analog thereof.

In one embodiment, the present invention provides a method of distributing a chemotherapeutic agent comprising distributing to a patient a predetermined amount of a first pharmaceutical composition comprising N-acetylcysteine, or a salt, solvate, prodrug, and/or analog thereof, in combination with an instruction of administering the first pharmaceutical composition with a predetermined amount of a second pharmaceutical composition comprising at least one additional active agent. In another embodiment, the present invention provides a method of distributing a chemotherapeutic agent comprising distributing to a patient a predetermined amount of a first pharmaceutical composition comprising at least one active agent, in combination with an instruction of administering the first pharmaceutical composition with a predetermined amount of a second pharmaceutical composition comprising N-acetylcysteine, or a salt, solvate, prodrug, and/or analog thereof.

EXAMPLES

The following examples are provided for illustrative purposes only. These examples should not be considered as limiting the invention in any way.

Example 1

FIG. 2 shows the configuration of the bi-layer matrix delivery system. The dosage form is composed of two layers, one being an immediate release layer and the other the sustained release layer. The immediate release layer (IR) comprises 84% of N-acetyl-L-cysteine, 5% of hydroxypropylmethylcellose E5, 5% of croscarmellose sodium, 5% of sodium bicarbonate and 1% of magnesium stearate, and the sustained release layer (SR) comprises 60% of N-acetyl-L-cysteine, 15% of a mixture of Carbomer 71G and Carbomer 934P, 24% of sodium bicarbonate and 1% of magnesium stearate. The system can be prepared as described below.

First, all these components are sieved individually through a 40-mesh screen. The sieved IR ingredients except Mg stearate are dry-blended in a V-blender for 10 minutes. The resultant dry blend is roller compacted using a roller compactor with a 1.25-mm screen. Then, the resultant IR layer granules are blended with 1% Mg stearate in the V-blender. Next, the SR granules are prepared using the same way as the IR granules. Finally, the 238 mg of the IR granules and 666.7 mg of the SR granules are compressed in to a bi-layer tablet on a bi-layer tablet press with 0.75"×0.35" oval tooling. Each of the bi-layer tablets comprises 600 mg of NAC in total, 200 mg in the IR layer and 400 mg in the SR layer. By adjusting the weight ratio of Carbomer 71G to Carbomer 934P in the SR layer, various release durations from 4 hr to 24 hrs can be achieved. The release duration here is referred to as the period of time during which 90% of NAC are released from the matrix tablet.

Example 2

The procedure for preparing the matrix tablet in this example is identical to that described in Example 1. However, the tablet in this example comprises N-acetyl-D-cysteine instead of N-acetyl-L-cysteine.

Example 3

The procedure for preparing the matrix tablet in this example is identical to that described in Example 1. However, the IR component of the tablet in this example comprises the racemate or any mixtures of N-acetyl-D-cysteine and N-acetyl-L-cysteine.

Example 4

The procedure for preparing the matrix tablet in this example is identical to that described in Example 1. However, the SR component of tablet in this example comprises an ester prodrug of N-acetyl-L-cysteine. The prodrug has the general chemical structure as shown in Scheme 2 (compounds C), wherein R can be methyl, ethyl, propyl, butyl, pentyl or hexyl.

Example 5

The procedure for preparing the matrix tablet in this example is identical to that described in Example 1. However, the SR component of the tablet in this example comprises an ester prodrug of N-acetyl-D-cysteine. The prodrug has the general chemical structure as shown in Scheme 2 (compounds D), wherein R can be methyl, ethyl, propyl butyl, pentyl or hexyl.

Example 6

The procedure for preparing the matrix tablet in this example is identical to that described in Example 1. However, the SR component of the tablet in this example comprises an amide prodrug of N-acetyl-L-cysteine. The prodrug has the chemical structure as shown in Scheme 2 (compounds E), wherein each $R^2$ is independently as described herein.

Example 7

The procedure for preparing the matrix tablet in this example is identical to that described in Example 1. However, the SR component of the tablet in this example comprises an amide prodrug of N-acetyl-D-cysteine. The prodrug has the chemical structure as shown in Scheme 2 (compounds F), wherein each $R^2$ is independently as described herein.

Example 8

The procedure for preparing the matrix tablet in this example is identical to that described in Example 1. However, the SR component of the tablet in this example comprises an anhydride prodrug of N-acetyl-L-cysteine. The prodrug has the chemical structure as shown in Scheme 2 (compounds G), wherein $R^3$ is as described herein.

Example 9

The procedure for preparing the matrix tablet in this example is identical to that described in Example 1. However, the SR component of the tablet in this example comprises an anhydride prodrug of N-acetyl-D-cysteine. The prodrug has the chemical structure as shown in Scheme 2 (compounds H), wherein $R^3$ is as described herein.

Example 10

The procedure for preparing the matrix tablet in this example is identical to that described in Example 1. However, the SR component of the tablet in this example comprises either (a) the dimer of N-acetylcysteine, DiNAC (compound I), (b) N-acetylcysteine L-lysinate (Nacystelyn, Compound J), or (c) Carbocisteine. (compound K).

Example 11

The procedure for preparing the matrix tablet in this example is identical to that described in Example 1. The tablet in this example has the following composition in the SR layer.

| Component | Weight % |
|---|---|
| NAC | 60 |
| HPMC E5 and HPMC K100M | 39 |
| Mg Stearate | 1 |

Example 12

The procedure for preparing the matrix tablet in this example is identical to that described in Example 1. The tablet in this example has the following composition in the SR layer.

| Component | Weight % |
|---|---|
| Any of Compounds A through K | 60 |
| Na bicarbonate | 0-34 |
| Chitosan | 5-39 |
| Mg Stearate | 1 |

Example 13

The procedure for preparing the matrix tablet in this example is identical to that described in Example 1. The tablet in this example has the following composition in the SR layer.

| Component | Weight % |
|---|---|
| Any of Compounds A through K | 60 |
| Na bicarbonate | 0-34 |
| Crosslinked high amylose starch | 5-39 |
| Mg Stearate | 1 |

Example 14

The procedure for preparing the matrix tablet in this example is identical to that described in Example 1. The tablet in this example has the following composition in the SR layer.

| Component | Weight % |
|---|---|
| NAC | 60 |
| Na bicarbonate | 0-34 |
| Polyox coagulant | 5-39 |
| Mg Stearate | 1 |

Example 15

FIG. 3 schematically shows the configuration of an osmotic delivery system for controlled release of NAC to the gastrointestinal tract of a human. An embodiment of this delivery system comprises the first immediate release drug layer, the second sustained release drug layer and the third osmotic push layer, and the rate-controlling membrane enrobing the three layers.

The delivery system is manufactured as follows: first, the immediate release NAC layer and the sustained release NAC layer granules are separately prepared by a roller compaction process as described in Example 1. Next, the osmotic push layer is prepared by a fluid-bed granulation process. Then, the first IR drug layer granules, the second SR drug layer granules and the osmotic push layer granules are compressed together to from a tri-layer table, using a $17/64$" tooling. A rate-controlling membrane composition is coated around the tri-layer tablet and a 155 mil orifice for drug release is formed by cutting through the membrane. The tables below list the amount of each component comprised in the osmotic delivery system.

| First IR Drug Layer | |
|---|---|
| Component | Amount (mg) |
| NAC | About 10-1500, usually 200 |
| Croscarmellose sodium | About 23.8 |
| HPMC E5 | About 11.9 |
| Mg Stearate | About 2.3 |

| Second SR Drug layer | |
|---|---|
| Compounds A to K, | up to 2400, usually 400 |
| HPMC K100M | About 22.5 |
| HPMC E5 | About 22.5 |
| Mg Stearate | About 4.5 |

| Third Osmotic Push Layer | |
|---|---|
| Sodium-Carboxylmethylcellulose | About 159 |
| Sodium Chloride | About 75 |
| HPMC E5 | About 12.5 |
| Mg stearate | About 1.3 |
| Ferric Oxide | About 2.5 |

| Rate-limiting Membrane | |
| --- | --- |
| Cellulose acetate (39.8% acetate content) | About 76.5 |
| Pluronic F68 | About 13.5 |

Example 16

FIG. 4 schematically shows the configuration of a delivery tablet for controlled release of NAC to the gastrointestinal tract in a human. The preferred embodiment of this tablet comprises IR particulates and SR spheres of NAC. The tablet will disintegrate in a gastric fluid, with the IR particulates dissolving rapidly and the SR spheres releasing NAC slowly.

The delivery system is manufactured as follows: first, the active NAC cores are prepared. NAC and Na bicarbonate are sieved through a 40-mesh screen and blended well to obtain a homogeneous powder mixture. The powder mixture is applied to non-pareil sugar spheres (preferred particle size of 420-500 μm) using a Freund CF granulator. A 10% solution of HPMC E5 in ethanol is used as a binding agent for this drug powder layering process. Then, the active cores are coated with a rate-controlling membrane composition. The uncoated active core also serves as the IR spheres. Finally, the IR spheres and the coated spheres are dry-blended with a disintegrant and compressed into a tablet using 0.75"×0.35" oval tooling. The tables below list the composition of this multiparticulate tablet.

| IR sphere | |
| --- | --- |
| Component | WT % |
| NAC or compounds A-K, or analogs | About 59.5 |
| Na Bicarbonate | About 3.5 |
| Non-Pareil | About 30.0 |
| HPMC | About 7.0 |

| SR sphere | |
| --- | --- |
| Component | Wt % |
| NAC | About 47.6 |
| Na Bicarbonate | About 2.8 |
| Non-Pareil | About 24 |
| HPMC | About 5.6 |
| Sreelease solid | About 20 |

| Multiparticulate Tablet | |
| --- | --- |
| Component | Wt % |
| IR spheres | About 27.1 |
| SR spheres | About 67.9 |
| Crosscarmellose Na | About 5.0 |

Example 17

Preparation of a Controlled Release Oral Dosage Form of a NAC Prodrug

The controlled release system is composed of a drug core and a release rate-controlling membrane. The drug core comprises 70% of the N-acetyl-L-cysteine prodrug, 19.0% of Puronic F127, 10% of Povidone $K_{29}$ and 1% of magnesium stearate. The membrane is composed of cellulose ether (ethyl cellulose or cellulose acetate) and a water flux enhancer (Povidone K90, PEG 400, or Pluronic F68). The system can be prepared as described below.

First, all these components are sieved individually through a 40-mesh screen. The sieved ingredients except Mg stearate are dry-blended in a V-blender for 10 mins. The resultant dry blend is roller compacted using a roller compactor with a 1.25-mm screen. Then, the resultant granules are blended with 1% Mg stearate in the V-blender. Next, 857.1 mg of the granules are compressed in to a tablet. Each tablet comprises 600 mg of the NAC prodrug. By adjusting either the weight ratio of the cellulose ether to the flux enhancer in the membrane or the membrane thickness, various release durations from 3 hr to 24 hrs can be achieved. The release duration here is referred to as the period of time during which 90% of NAC are released from the delivery system.

All publications, patents, and patent applications referenced herein (including the references listed herein below) are incorporated by reference in their entireties to the same extent as if each individual publication, patent, or patent application was specifically and individually indicated to be incorporated by reference in its entirety.

References

1. Zambon A, Gervois P, Pauletto P, Fruchart J C, Staels B. Modulation of hepatic inflammatory risk markers of cardiovascular diseases by PPAR-alpha activators: clinical and experimental evidence. *Arterioscler Thromb Vasc Biol*. May 2006; 26(5):977-986.
2. Wilson A M, Ryan M C, Boyle A J. The novel role of C-reactive protein in cardiovascular disease: risk marker or pathogen. *Int J Cardiol*. Jan. 26, 2006; 106(3):291-297.
3. Mora S, Ridker P M. Justification for the Use of Statins in Primary Prevention: an Intervention Trial Evaluating Rosuvastatin (JUPITER)—can C-reactive protein be used to target statin therapy in primary prevention? *Am J Cardiol*. Jan. 16, 2006; 97(2A):33A-41A.
4. Paffen E, DeMaat M P. C-reactive protein in atherosclerosis: A causal factor? *Cardiovasc Res*. Jul. 1, 2006; 71(1): 30-39.
5. Inoue N. Vascular C-reactive protein in the pathogenesis of coronary artery disease: role of vascular inflammation and oxidative stress. *Cardiovasc Hematol Disord Drug Targets*. December 2006; 6(4):227-231.
6. de Ferranti S D, Rifai N. C-reactive protein: a nontraditional serum marker of cardiovascular risk. *Cardiovasc Pathol*. January-February 2007; 16(1):14-21.
7. Gotto A M, Jr. Role of C-reactive protein in coronary risk reduction: focus on primary prevention. *Am J Cardiol*. Mar. 1, 2007; 99(5):718-725.
8. Bisoendial R J, Kastelein J J, Stroes E S. C-reactive protein and atherogenesis: from fatty streak to clinical event. *Atherosclerosis*. December 2007; 195(2):e10-18.
9. Gonzalez-Gay M A, Gonzalez-Juanatey C, Pineiro A, Garcia-Porrua C, Testa A, Llorca J. High-grade C-reactive protein elevation correlates with accelerated atherogenesis in patients with rheumatoid arthritis. *J Rheumatol*. July 2005; 32(7):1219-1223.
10. Venugopal S K, Devaraj S, Jialal I. Effect of C-reactive protein on vascular cells: evidence for a proinflammatory, proatherogenic role. *Curr Opin Nephrol Hypertens*. January 2005; 14(1):33-37.
11. Jialal I, Devaraj S, Venugopal S K. C-reactive protein: risk marker or mediator in atherothrombosis? *Hypertension*. July 2004; 44(1):6-11.

12. Chang J W, Kim C S, Kim S B, Park S K, Park J S, Lee S K. C-reactive protein induces NF-kappaB activation through intracellular calcium and ROS in human mesangial cells. *Nephron Exp Nephroi.* 2005; 101(4):e165-172.
13. Fu A L, Dong Z H, Sun M I. Protective effect of N-acetyl-L-cysteine on amyloid beta-peptide-induced learning and memory deficits in mice. *Brain Res.* Sep. 13, 2006; 1109(1):201-206.
14. Hicdonmez T, Kanter M, Tiryaki M, Parsak T, Cobanoglu S, Neuroprotective effects of N-acetylcysteine on experimental closed head trauma in rats. *Neurochem Res.* April 2006; 31(4):473-481.
15. Jara-Prado A, Ortega-Vazquez A, Martinez-Ruano L, Rios C, Santamaria A. Homocysteine-induced brain lipid peroxidation: effects of NMDA receptor blockade, antioxidant treatment, and nitric oxide synthase inhibition. *Neurotox Res.* 2003; 5(4):237-243.
16. Karageorgos N, Patsoukis N, Chroni E, Konstantinou D, Assimakopoulos S F, Georgiou C. Effect of N-acetylcysteine, allopurinol and vitamin E on jaundice-induced brain oxidative stress in rats. *Brain Res.* Sep. 21, 2006; 1111(1): 203-212.
17. Penugonda S, Mare S, Goldstein G, Banks W A, Ercal N. Effects of N-acetylcysteine amide (NACA), a novel thiol antioxidant against glutamate-induced cytotoxicity in neuronal cell line PC12. *Brain Res.* Sep. 21, 2005; 1056(2): 132-138.
18. Price T O, Uras F, Banks W A, Ercal N. A novel antioxidant N-acetylcysteine amide prevents gp120- and Tat-induced oxidative stress in brain endothelial cells. *Exp Neurol.* September 2006; 201(1):193-202.
19. Shea TB. Effects of dietary supplementation with N-acetyl cysteine, acetyl-L-carnitine and S-adenosyl methionine on cognitive performance and aggression in normal mice and mice expressing human ApoE4. *Neuromolecular Med.* 2007; 9(3):264-269.
20. Tchantchou F, Graves M, Ortiz D, Rogers E, Shea T B. Dietary supplementation with 3-deaza adenosine, N-acetyl cysteine, and S-adenosyl methionine provide neuroprotection against multiple consequences of vitamin deficiency and oxidative challenge: relevance to age-related neurodegeneration. *Neuromolecular Med.* 2004; 6(2-3):93-103.
21. Kaya H, Koc A, Sogut S, et al. The protective effect of N-acetylcysteine against cyclosporine A-induced hepatotoxicity in rats. *J Appl Toxicol.* January-February 2008; 28(1):15-20.
22. Liu Y, Zhang H, Zhang L, et al. Antioxidant N-acetylcysteine attenuates the acute liver injury caused by X-ray in mice. *Eur J Pharmacol.* Dec. 1, 2007; 575(1-3):142-148.
23. Alipour M, Omri A, Smith M G, Suntres Z E. Prophylactic effect of liposomal N-acetylcysteine against LPS-induced liver injuries. *J Endotoxin Res.* 2007; 13(5):297-304.
24. Koksel O, Cinel I, Tamer L, et al. N-acetylcysteine inhibits peroxynitrite-mediated damage in oleic acid-induced lung injury. *Pulm Pharmacol Ther.* 2004; 17(5):263-270.
25. Chuang I C, Liu D D, Kao S J, Chen H I. N-acetylcysteine attenuates the acute lung injury caused by phorbol myristate acetate in isolated rat lungs. *Pulm Pharmacol Ther.* 2007; 20(6):726-733.
26. Chen C M, Yin M C, Hsu C C, Liu T C. Antioxidative and anti-inflammatory effects of four cysteine-containing agents in striatum of MPTP-treated mice. *Nutrition.* July-August 2007; 23(7-8):589-597.
27. Van Antwerpen P, Boudjeltia K Z, Babar S, et al. Thiol-containing molecules interact with the myeloperoxidase/H2O2/chloride system to inhibit LDL oxidation. *Biochem Biophys Res Commun.* Nov. 11, 2005; 337(1):82-88.
28. Rattan A K, Arad Y. Temporal and kinetic determinants of the inhibition of LDL oxidation by N-acetylcysteine (NAC). *Atherosclerosis.* June 1998; 138(2):319-327.
29. Galis Z S, Asanuma K, Godin D, Meng X. N-acetylcysteine decreases the matrix-degrading capacity of macrophage-derived foam cells: new target for antioxidant therapy? *Circulation.* Jun. 23, 1998; 97(24):2445-2453.
30. Fujii H, Li S H, Szmitko P E, Fedak P W, Verma S. C-reactive protein alters antioxidant defenses and promotes apoptosis in endothelial progenitor cells. *Arterioscler Thromb Vasc Biol.* November 2006; 26(11):2476-2482.
31. Krieger M H, Santos K F, Shishido S M, et al. Antiatherogenic effects of S-nitroso-N-acetylcysteine in hypercholesterolemic LDL receptor knockout mice. *Nitric Oxide.* February 2006; 14(1):12-20.
32. Ivanovski O, Szumilak D, Nguyen-Khoa T, et al. The antioxidant N-acetylcysteine prevents accelerated atherosclerosis in uremic apolipoprotein E knockout mice. *Kidney Int.* June 2005; 67(6):2288-2294.
33. Wagberg M, Jansson A H, Westerlund C, et al. N,N'-diacetyl-L-cystine (DiNAC), the disulphide dimer of N-acetylcysteine, inhibits atherosclerosis in WHHL rabbits: evidence for immunomodulatory agents as a new approach to prevent atherosclerosis. *J Pharmacol Exp Ther.* October 2001; 299(1):76-82.
34. Prasad K. C-reactive protein (CRP)-lowering agents. *Cardiovasc Drug Rev.* Spring 2006; 24(1):33-50.
35. Devaraj S, Rogers J, Jialal I. Statins and biomarkers of inflammation. *Curr Atheroscler Rep.* January 2007; 9(1): 33-41.
36. Nissen S E. Effect of intensive lipid lowering on progression of coronary atherosclerosis: evidence for an early benefit from the Reversal of Atherosclerosis with Aggressive Lipid Lowering (REVERSAL) trial. *Am J Cardiol.* Sep. 5, 2005; 96(5A):61F-68F.
37. Molnar Z, Szakmany T, Koszegi T. Prophylactic N-acetylcysteine decreases serum CRP but not PCT levels and microalbuminuria following major abdominal surgery. A prospective, randomised, double-blinded, placebo-controlled clinical trial. *Intensive Care Med.* May 2003; 29(5): 749-755.
38. Zuin R, Palamidese A, Negrin R, Catozzo L, Scarda A, Balbinot M. High-dose N-acetylcysteine in patients with exacerbations of chronic obstructive pulmonary disease. *Clin Drug Investig.* 2005; 25(6):401-408.
39. Aoyama K, Matsumura N, Watabe M, Nakaki T. Oxidative stress on EAAC1 is involved in MPTP-induced glutathione depletion and motor dysfunction. *Eur J Neurosci.* Dec. 14, 2007.
40. Shavali S, Sens D A. Synergistic Neurotoxic Effects of Arsenic and Dopamine in Human Dopaminergic Neuroblastoma SH-SY5Y Cells. *Toxicol Sci.* Dec. 13, 2007.
41. Kim-Han J S, O'Malley K L. Cell stress induced by the parkinsonian mimetic, 6-hydroxydopamine, is concurrent with oxidation of the chaperone, ERp57, and aggresome formation. *Antioxid Redox Signal.* December 2007; 9(12): 2255-2264.
42. U.S. Pat. No. 4,612,008
43. U.S. Pat. No. 4,894,240
44. U.S. Pat. No. 4,871,548
45. Sjödin K, Nilsson E, Hallberg A, Tunek A. Metabolism of N-acetyl-L-cysteine. Some structural requirements for the deacetylation and consequences for the oral bioavailability, *Biochem Pharmacol.* 1989 Nov. 15; 38(22):3981-5

We claim:

1. A composition in an oral dosage form comprising a sustained release (SR) component, wherein the SR component comprises ethyl ester of N-acetylcysteine, or a salt or solvate thereof;
further comprising an immediate release (IR) component, wherein the IR component comprises an ethyl ester of N-acetylclysteine or a salt or solvate thereof; and
wherein the composition, upon oral administration, provides a therapeutically effective plasma concentration of N-acetylcysteine over more than about 2 hours following the administration.

2. The composition of claim 1,
wherein the composition, upon oral administration, provides a therapeutically effective plasma concentration of N-acetylcysteine over about 30 minutes to about 24 hours following the administration.

3. The composition of claim 2, wherein the SR and/or IR component is absorbable in the lower gastrointestinal tract of a mammal.

4. The composition of claim 1, wherein the SR component comprises a matrix, wherein the matrix comprises:
ethyl ester of N-acetylcysteine, or a salt solvate thereof; and
a release rate controlling polymer.

5. The composition of claim 1, comprising
a layer of the IR component, and
a layer of the SR component, wherein the SR component comprises a matrix comprising ethyl ester of N-acetylcysteine, or a salt or solvate thereof; and a release rate controlling polymer.

6. The composition of claim 5, wherein the rate controlling polymer is a hydrophilic polymer.

7. The composition of claim 6, wherein the hydrophilic polymer is selected from the group consisting of polyethylene oxide, hydroxypropyl cellulose, hydroxypropyl methyl cellulose, hydroxyethyl cellulose, sodium carboxymethylcellulose, calcium carboxymethyl cellulose, methyl cellulose, polyacrylic acid, maltodextrin, pre-gelatinized starch, guar gum, sodium alginate, polyvinyl alcohol, chitosan, locust bean gum, amylase and a combination thereof.

8. The composition of claim 1, comprising a release rate controlling membrane disposed over:
a pull layer comprising ethyl ester of N-acetylcysteine, or a salt or solvate thereof, and
an osmotic push layer;
wherein the release rate controlling membrane has an orifice immediately adjacent to the pull layer.

9. The composition of claim 8, wherein the pull layer further comprises a release rate controlling polymer.

10. The composition of claim 1, comprising a release rate controlling membrane disposed over:
a first pull layer comprising the IR component,
a second pull layer comprising the SR component, and
an osmotic push layer;
wherein the release rate controlling membrane has an orifice immediately adjacent to the first pull layer.

11. The composition of claim 10, wherein the SR component comprises a matrix comprising:
ethyl ester of N-acetylcysteine, or a salt or solvate thereof; and
a release rate controlling polymer.

12. The composition of claim 11, wherein the release rate controlling polymer is a hydrophilic polymer.

13. The composition of claim 12, wherein the hydrophilic polymer is selected from the group consisting of polyethylene oxide, hydroxypropyl cellulose, hydroxypropyl methyl cellulose, hydroxyethyl cellulose, sodium carboxymethylcellulose, calcium carboxymethyl cellulose, methyl cellulose, polyacrylic acid, maltodextrin, pre-gelatinized starch, guar gum, sodium alginate, polyvinyl alcohol, chitosan, locust bean gum, amylase and a combination thereof.

14. The composition of claim 10, wherein the release rate controlling membrane comprises a water insoluble and non-erodable polymer.

15. The composition of claim 14, wherein the water insoluble and non-erodable polymer is selected from the group consisting of a cellulose ester, a cellulose ether, a cellulose ester-ether, and a combination thereof.

16. The composition of claim 14, wherein the water insoluble and non-erodable polymer is selected from the group consisting of cellulose acylate, cellulose diacylate, cellulose triacylate, cellulose acetate, cellulose diacetate, cellulose triacetate, a monocellulose alkanylate, a dicellulose alkanylate, a tricellulose alkanylate, a monocellulose aroylate, a dicellulose aroylate a tricellulose aroylate, and a combination thereof.

17. The composition of claim 10, wherein the osmotic push layer comprises an osmopolymer.

18. The composition of claim 17, wherein the osmopolymer is selected from the group consisting of poly(hydroxyalkylmethacrylate) having a molecular weight of from about 30,000 to about 5,000,000; poly(vinylpyrrolidone) having molecular weight of from about 10,000 to 360,000 about; anionic and cationic hydrogels; polyelectrolyte complexes; poly(vinyl alcohol); a mixture of methyl cellulose, crosslinked agar, and carboxymethyl cellulose; a copolymer of maleic anhydride with styrene, ethylene, propylene, butylene or isobutylene; N-vinyl lactams; Carbopol; acidic carboxy polymers having a molecular weight from about 450,000 to about 4,000,000; a sodium salt of Carbopol; acidic carboxy polymers and/or the metal salts thereof; polyethylene oxide polymers having a molecular weight from about 100,000 to about 7,500,000; and combinations thereof.

19. The composition of claim 10, wherein the pull layer comprises an osmagent.

20. The composition of claim 19, wherein the osmagent is selected from the group consisting of a magnesium sulfate, magnesium chloride, sodium chloride, potassium chloride, lithium chloride, potassium sulfate, sodium sulfate, lithium sulfate, lithium phosphate, sodium phosphate, potassium phosphate, potassium acid phosphate, calcium lactate, mannitol, urea, inositol, magnesium succinate, tartaric acid, carbohydrates such as raffinose, sucrose, glucose, lactose monohydrate, and a blend of fructose glucose.

21. The composition of claim 1, wherein the SR component comprises one or more particles, and each of the particles comprises
an active core comprising ethyl ester of N-acetylcysteine, or a salt or solvate thereof; and
a release rate controlling polymer disposed over the core.

22. The composition of claim 1, wherein the SR component comprises one or more particles, and each of the particles comprises
an inert core,
an active layer comprising ethyl ester of N-acetylcysteine, or a salt or solvate thereof disposed over the inert core, and
a release rate controlling polymer disposed over the active layer.

23. The composition of claim 1, wherein
the IR component comprises one or more particles, and
the SR component comprises one or more particles, and each of the particles of the SR component comprises an active core comprising ethyl ester of N-acetylcysteine, or a salt or solvate thereof; and
a release rate controlling polymer disposed over the core.

24. The composition of claim 1, wherein
the IR component comprises one or more particles, and
the SR component comprises one or more particles, and
each of the particles of the SR component comprises
an inert core,
an active layer comprising ethyl ester of N-acetylcysteine, or a salt or solvate thereof disposed over the inert core, and
a release rate controlling polymer disposed over the active layer.

25. The composition of claim 24, wherein the release rate controlling polymer comprises a film-forming, water insoluble polymer in combination with a film-forming, water soluble polymer.

26. The composition of claim 25, wherein the film-forming, water insoluble polymer is selected from the group consisting of ethylcellulose, cellulose acetate, cellulose propionate (lower, medium or higher molecular weight), cellulose acetate propionate, cellulose acetate butyrate, cellulose acetate phthalate, cellulose triacetate, poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), poly(ethylene), poly(ethylene) low density, poly(ethylene) high density, poly(propylene), poly(ethylene oxide), poly(ethylene terephthalate), poly(vinyl isobutyl ether), poly(vinyl acetate), poly(vinyl chloride), polyurethane, and combinations thereof.

27. The composition of claim 25, wherein the film-forming, water soluble polymer is selected from the group consisting of polyvinyl alcohol, polyvinylpyrrolidone, methyl cellulose, hydroxypropyl cellulose, hydroxypropylmethyl cellulose and polyethylene glycol, Pluronic F108, Pluronic F127, Pluronic F68, and combinations thereof.

28. The composition of claim 24, wherein each of the particles of the IR component comprises:
an inert core, and
a coating disposed over the inert core,
wherein the coating comprises ethyl ester of N-acetylcysteine, or a salt or solvate thereof.

29. A composition in an oral dosage form comprising a sustained release (SR) component, wherein the SR component comprises
ethyl ester of N-acetylcysteine, or a salt or solvate thereof; and
a release rate controlling polymer.

30. A method of treating inflammation in a mammal comprising orally administering to the mammal the composition of claim 1.

31. The method of claim 30, wherein the inflammation is liver inflammation caused by acetaminophen.

32. A process of making a composition of claim 1 comprising the steps of
applying forces to loose solids comprising ethyl ester of N-acetylcysteine, or a salt or solvate thereof, thereby obtaining a solid sheet;
reducing the size of the solid sheet, thereby obtaining granules; and
forming the granules into the SR and/or IR component of claim 1.

33. The process of claim 32, wherein the process the process does not utilize a solvent.

34. The process of claim 33, wherein the applying step is carried out by pressing the loose solids between two counter rotating rolls.

35. The composition of claim 1, further comprising
at least one additional active agent.

36. The composition of claim 35, wherein the at least one additional active agent is a statin.

37. The composition of claim 36, wherein the statin is selected from the group consisting of atorvastatin, cerivastatin, fluvastatin, lovastatin, mevastatin, pitavastatin, pravastatin, rosuvastatin, simvastatin, and a combination thereof.

38. The composition of claim 1, wherein the composition, upon oral administration, provides a therapeutically effective plasma concentration of N-acetylcysteine over more than about 4 hours following the administration.

39. The composition of claim 1, wherein the composition, upon oral administration, provides a therapeutically effective plasma concentration of N-acetylcysteine over about 2 to about 24 hours following the administration.

40. The composition of claim 1, wherein the ethyl ester of N-acetylcysteine has a structure:

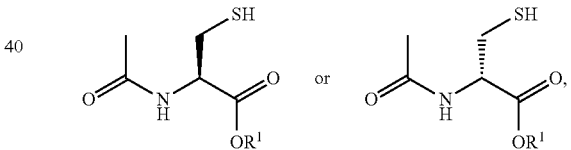

wherein $R^1$ is ethyl.

41. The composition of claim 35, wherein the at least one additional active agent is acetaminophen.

42. A method of treating inflammation in a mammal, comprising orally administering to the mammal the composition of claim 1.

43. The method of claim 42, wherein the inflammation is liver inflammation caused by acetaminophen.

* * * * *